US006800472B2

(12) United States Patent
Canfield et al.

(10) Patent No.: US 6,800,472 B2
(45) Date of Patent: Oct. 5, 2004

(54) EXPRESSION OF LYSOSOMAL HYDROLASE IN CELLS EXPRESSING PRO-N-ACETYLGLUCOSAMINE-1-PHOSPHODIESTER α-N-ACETYL GLUCOSIMANIDASE

(75) Inventors: William Canfield, Oklahoma City, OK (US); Stuart Kornfeld, Saint Louis, MO (US)

(73) Assignee: Genzyme Glycobiology Research Institute, Inc., Oklahoma City, OK (US)

( * ) Notice: Subject to any disclaimer, the term of this patent is extended or adjusted under 35 U.S.C. 154(b) by 0 days.

(21) Appl. No.: 10/023,894

(22) Filed: Dec. 21, 2001

(65) Prior Publication Data

US 2003/0143669 A1 Jul. 31, 2003

(51) Int. Cl.$^7$ .............................. C12N 9/14; C12N 9/24
(52) U.S. Cl. ....................................... 435/195; 435/200
(58) Field of Search .................................. 435/195, 200

(56) References Cited

U.S. PATENT DOCUMENTS

| | | | |
|---|---|---|---|
| 3,957,578 A | 5/1976 | Narita et al. |
| 3,966,555 A | 6/1976 | Arnaud et al. |
| 3,972,777 A | 8/1976 | Yamada et al. |
| 4,140,107 A | 2/1979 | Lancee et al. |
| 4,156,013 A | 5/1979 | Bruinvels et al. |
| 4,195,126 A | 3/1980 | Hall |
| 4,328,215 A | 5/1982 | Bueding |
| 4,332,894 A | 6/1982 | Whistler |
| 4,401,662 A | 8/1983 | Lormeau et al. |
| 4,401,758 A | 8/1983 | Lormeau et al. |
| 4,431,737 A | 2/1984 | Olivieri et al. |
| 4,433,946 A | 2/1984 | Christianson et al. |
| 4,452,794 A | 6/1984 | Kort et al. |
| 4,474,770 A | 10/1984 | Lormeau et al. |
| 4,492,761 A | 1/1985 | Durack |
| 4,496,722 A | 1/1985 | Gallop et al. |
| 4,595,015 A | 6/1986 | Jansen et al. |
| 4,615,884 A | 10/1986 | Harshman |
| 4,639,420 A | 1/1987 | Schaffner |
| 4,659,817 A | 4/1987 | Gallop et al. |
| 4,749,570 A | 6/1988 | Poznansky |
| 4,798,169 A | 1/1989 | Rosen et al. |
| 4,851,390 A | 7/1989 | Morishige |
| 4,866,042 A | 9/1989 | Neuwelt |
| 4,975,441 A | 12/1990 | Gibson |
| 4,981,801 A | 1/1991 | Suzuki et al. |
| 4,986,274 A | 1/1991 | Stephens |
| 4,987,223 A | 1/1991 | Choay et al. |
| 4,997,760 A | 3/1991 | Hirabayashi et al. |
| 5,001,072 A | 3/1991 | Olson |
| 5,015,470 A | 5/1991 | Gibson |
| 5,055,401 A | 10/1991 | Liljestrom et al. |
| 5,060,428 A | 10/1991 | Arthur, Jr. et al. |
| 5,061,025 A | 10/1991 | Mattes et al. |
| 5,075,231 A | 12/1991 | Moreau et al. |
| 5,077,200 A | 12/1991 | Habenstein |
| 5,082,778 A | 1/1992 | Overbeeke et al. |
| 5,089,392 A | 2/1992 | Miller et al. |
| 5,126,247 A | 6/1992 | Palmer et al. |
| 5,143,841 A | 9/1992 | Hirabayashi et al. |
| 5,166,320 A | 11/1992 | Wu et al. |
| 5,179,023 A | 1/1993 | Calhoun et al. |
| 5,202,253 A | 4/1993 | Esmon et al. |
| 5,205,917 A | 4/1993 | Klock, Jr. |
| 5,208,148 A | 5/1993 | Haugland et al. |
| 5,217,865 A | 6/1993 | Myerowitz |
| 5,242,805 A | 9/1993 | Naleway et al. |
| 5,260,447 A | 11/1993 | Nakajima et al. |
| 5,281,394 A | 1/1994 | Holub |
| 5,296,365 A | 3/1994 | Overbeeke et al. |
| 5,310,646 A | 5/1994 | Whitley |
| 5,316,906 A | 5/1994 | Haugland et al. |
| 5,344,352 A | 9/1994 | Horne et al. |
| 5,356,804 A | 10/1994 | Desnick et al. |
| 5,362,628 A | 11/1994 | Haugland |
| 5,366,883 A | 11/1994 | Asada et al. |
| 5,382,524 A | 1/1995 | Desnick et al. |
| 5,401,650 A | 3/1995 | Desnick et al. |
| 5,405,751 A | 4/1995 | Roncarolo |
| 5,420,112 A | 5/1995 | Lewis et al. |
| 5,433,946 A | 7/1995 | Allen, Jr. et al. |
| 5,439,935 A | 8/1995 | Rawlings et al. |

(List continued on next page.)

FOREIGN PATENT DOCUMENTS

WO           99/31117          6/1999

OTHER PUBLICATIONS

Do, H. et al. Human Mannose 6–Phosphate–uncovering Enzyme is Synthesized as a Proenzyme that is Activated by the Endoprotease Furin. Aug. 2002, J. Biol. Chem., vol. 277, No. 33, pp. 29737–29744.

Lee, W.S., et al., Multiple Signals Regulate Trafficking of the Mannose 6–Phosphate–uncovering Enayme. Feb. 2002, J. Biol. Chem., vol. 277, No. 5, pp. 3544–3551.

Alan D. Elbein et al, "Kifunensine, a Potent Inhibitor of the Glycoprotein Processing Mannosidase I", The Journal of Biological Chemistry, vol. 265, No. 26, Issue of Sep. 15, pp. 15599–15605, 1990.

Sly, "The Missing Link in Lysosomal Enzyme Targeting", The Journal of Clinical Investigation, vol. 105, No. 5, pp. 563–564, Mar. 2000.

(List continued on next page.)

*Primary Examiner*—Charles L. Patterson, Jr.
(74) *Attorney, Agent, or Firm*—Oblon, Spivak, McClelland, Maier & Neustadt, P.C.

(57) ABSTRACT

The present invention provides methods of producing a pro-N-acetylglucosamine-1-phosphodiester α N-acetyl glucosimanidase (phosphodiester α-GlcNAcase), in mammalian cells deficient in the furin proteolytic enzyme and methods of making lysosomal hydrolases having an N-acetylglucosamine-1-phosphate.

36 Claims, 3 Drawing Sheets

U.S. PATENT DOCUMENTS

Figure 1:
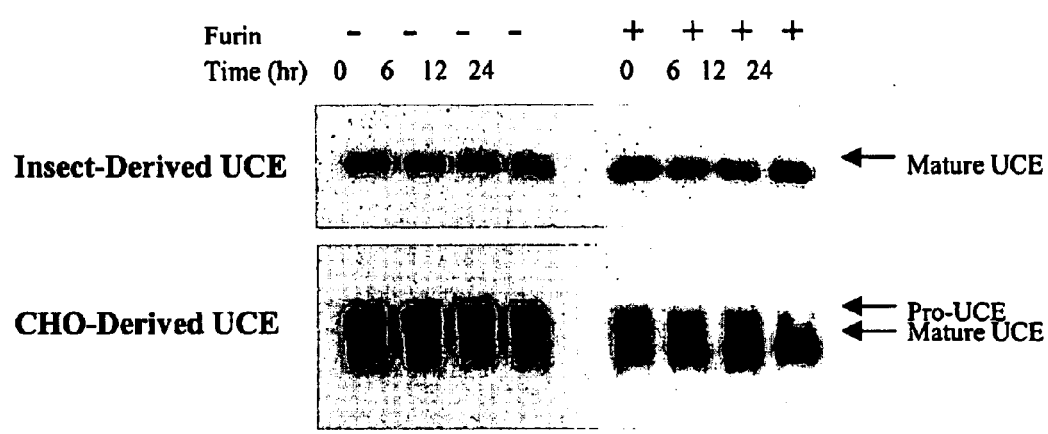

| | | |
|---|---|---|
| 5,443,986 A | 8/1995 | Haughland et al. |
| 5,449,604 A | 9/1995 | Schellenberg et al. |
| 5,466,809 A | 11/1995 | Dime |
| 5,475,095 A | 12/1995 | Myerowitz |
| 5,491,075 A | 2/1996 | Desnick et al. |
| 5,494,810 A | 2/1996 | Barany et al. |
| 5,501,957 A | 3/1996 | Dennis et al. |
| 5,512,471 A | 4/1996 | Smith |
| 5,534,615 A | 7/1996 | Baker et al. |
| 5,545,402 A | 8/1996 | Watkinson |
| 5,554,366 A | 9/1996 | Rawlings et al. |
| 5,565,362 A | 10/1996 | Rosen |
| 5,569,648 A | 10/1996 | Lewis et al. |
| 5,571,675 A | 11/1996 | Baker et al. |
| 5,571,893 A | 11/1996 | Baker et al. |
| 5,576,424 A | 11/1996 | Mao et al. |
| 5,578,479 A | 11/1996 | Laderman et al. |
| 5,580,757 A | 12/1996 | Desnick et al. |
| 5,583,160 A | 12/1996 | Igarashi et al. |
| 5,585,247 A | 12/1996 | Habenstein |
| 5,612,206 A | 3/1997 | Valerio et al. |
| 5,621,106 A | 4/1997 | Dime |
| 5,624,806 A | 4/1997 | Baker et al. |
| 5,627,073 A | 5/1997 | Baker et al. |
| 5,627,171 A | 5/1997 | Park et al. |
| 5,633,228 A | 5/1997 | Lewis et al. |
| 5,633,261 A | 5/1997 | Dime |
| 5,635,383 A | 6/1997 | Wu et al. |
| 5,639,607 A | 6/1997 | Desnick et al. |
| 5,639,939 A | 6/1997 | McCune, III |
| 5,648,229 A | 7/1997 | Habenstein |
| 5,648,335 A | 7/1997 | Lewis et al. |
| 5,658,567 A | 8/1997 | Calhoun et al. |
| 5,663,076 A | 9/1997 | Rostoker et al. |
| 5,663,254 A | 9/1997 | Lee et al. |
| 5,665,366 A | 9/1997 | Rawlings et al. |
| 5,679,545 A | 10/1997 | Baker et al. |
| 5,686,240 A | 11/1997 | Schuchman et al. |
| 5,691,181 A | 11/1997 | Lowe |
| 5,693,622 A | 12/1997 | Wolff et al. |
| 5,696,001 A | 12/1997 | Habenstein |
| 5,704,910 A | 1/1998 | Humes |
| 5,707,865 A | 1/1998 | Kohn et al. |
| 5,716,614 A | 2/1998 | Katz et al. |
| 5,719,031 A | 2/1998 | Haugland et al. |
| 5,721,367 A | 2/1998 | Kay et al. |
| 5,723,585 A | 3/1998 | Baker et al. |
| 5,728,381 A | 3/1998 | Wilson et al. |
| RE35,770 E | 4/1998 | Lormeau et al. |
| 5,736,360 A | 4/1998 | Gaulton et al. |
| 5,741,957 A | 4/1998 | Deboer et al. |
| 5,750,172 A | 5/1998 | Meade et al. |
| 5,759,775 A | 6/1998 | Caras et al. |
| 5,773,236 A | 6/1998 | Diwu et al. |
| 5,773,278 A | 6/1998 | Schuchman et al. |
| 5,792,647 A | 8/1998 | Roseman et al. |
| 5,798,239 A | 8/1998 | Wilson et al. |
| 5,798,366 A | 8/1998 | Platt et al. |
| 5,798,448 A | 8/1998 | Caras et al. |
| 5,807,943 A | 9/1998 | Lee et al. |
| 5,830,711 A | 11/1998 | Barany et al. |
| 5,830,850 A | 11/1998 | Gelb et al. |
| 5,830,916 A | 11/1998 | Hannun et al. |
| 5,840,578 A | 11/1998 | Desnick et al. |
| 5,849,885 A | 12/1998 | Nuyens et al. |
| 5,851,782 A | 12/1998 | Hannun et al. |
| 5,854,207 A | 12/1998 | Lee et al. |
| 5,858,351 A | 1/1999 | Podsakoff et al. |
| 5,858,744 A | 1/1999 | Baum et al. |
| 5,858,755 A | 1/1999 | Lowe |
| 5,861,491 A | 1/1999 | Nuijens et al. |
| 5,871,946 A | 2/1999 | Lucas et al. |
| 5,874,297 A | 2/1999 | Wu et al. |
| 5,879,937 A | 3/1999 | Roncarolo |
| 5,895,833 A | 4/1999 | Berg |
| 5,906,817 A | 5/1999 | Moullier et al. |
| 5,911,704 A | 6/1999 | Humes |
| 5,912,146 A | 6/1999 | Nishimura et al. |
| 5,914,231 A | 6/1999 | Hennink et al. |
| 5,916,870 A | 6/1999 | Lee et al. |
| 5,916,911 A | 6/1999 | Shayman et al. |
| 5,917,122 A | 6/1999 | Byrne |
| 5,919,690 A | 7/1999 | Knap et al. |
| 5,919,913 A | 7/1999 | Nuyens et al. |
| 5,928,928 A | 7/1999 | Aerts |
| 5,929,036 A | 7/1999 | McEver |
| 5,929,304 A | 7/1999 | Radin et al. |
| 5,932,211 A | 8/1999 | Wilson et al. |
| 5,939,279 A | 8/1999 | Smith |
| 5,968,502 A | 10/1999 | Treco et al. |
| 6,118,045 A | 9/2000 | Reuser et al. |

OTHER PUBLICATIONS

Raas–Rothschild et al., "Molecular Basis of Variant Pseudo–Hurler Polydystrophy (Mucolipidosis IIIC)", The Journal of Clinical Investigation, vol, 105, No. 5, pp. 673–681, Mar. 2000.

Bao et al., "Bovine Udp–N–Acetylglucosamine: Lysosomal–Enzyme N–Acetylglucosamine–1–Phosphotransferase", The Journal of Biological Chemistry, vol. 271, No. 49, pp. 31446–31451, Dec. 6, 1996.

Kornfield, "Purification and Multimeric Structure of Bovine N–Acetylglucosamine–1–Phosphodiester α–N–Acetylglucosaminidase", The Journal of Biological Chemistry, vol. 273, No. 36, pp. 23203–23210, Sep. 4, 1998.

Joan M. Moehring et al., "Strains of CHO–K1 Cells Resistant to *Pseudomonas* Exotoxin A and Cross–Resistant to Diphtheria Toxin and Viruses", Infection and Immunity, vol. 41., No. 3, Sep. 1983, pp. 998–1009.

Maxime Lehmann et al., "Lack of integrin α–chain endoproteolytic cleavage in furin–deficient human colon adenocarcinoma cells LoVo", Biochem. J. (1996) 317, 803–809.

Joseph F. Sucic et al., "Endoprotease PACE4 is $Ca^{2+-}$ dependent and temperature–sensitive and can partly rescue the phenotype of a furindeficient cell strain", Biochem. J. (1999) 339, pp. 639–647.

Valery M. Gordon et al., "Proteolytic Activation of Bacterial Toxins by Eukaryotic Cells Is Performed by Furin and by Additional Cellular Proteases", Infection and Immunity, vol. 63, Jan. 1995, pp. 82–87.

Noel M. Inocencio et al., "Endoprotease Activities Other Than Furin and PACE4 with a Role in Processing of HIV–I gp160 Glycoproteins in CHO–K1 Cells", JBC Online, vol. 272, No. 2, Jan. 10, 1997, pp. 1344–1348.

Valery M. Gordon et al., "Proteolytic Activation of Bacterial Toxins by Eukaryotic Cells Is Performed by Furin and by Additional Cellular Proteases", Infection and Immunity, vol. 63, No. 1, Jan. 1995, pp. 82–87.

John L. Middlebrook et al., "Response of cultured mammalian cells to the exotoxins of *Pseudomonas aeruginosa* and Corynebacterium diphtheriae: defferential cytotoxicity", Can. J. Microbiol. vol. 23, (1997), pp. 183–189.

Barbara H. Iglewski et al., "Mechanism of Action of *Pseudomonas aeruginosa* Exotoxin A: Adenosine Diphosphate–Ribosylation of Mammalian Elongation Factor 2 In Vitro and In Vivo", Infection and Immunity, vol. 15, No. 1, Jan. 1977, pp. 138–144.

Ayoubi Ta et al., "Production of recombinant proteins in Chinese hamster ovary cells overexpressing the subtilisin–like proprotein converting enzyme furin", NCBI, Mol Biol. Rep 1996:23(2):87–95.

Valery M. Gordon et al., "A Role for PACE4 in the proteolytic Activation of Anthras Toxin Protective Antigen", Infection and Immunity, vol. 65, No. 8, Aug. 1997 pp. 3370–3375.

R.O. Brady, et al., "Modifying Exogenous Glucocerebrosidase for Effective Replacement Therapy in Gaucher Disease", J. Inher. Metab. Des., vol. 17, (1994), pp. 510–519.

Emil D. Kakkis, et al., "Overexpression of the Human Lysosomal Enzyme α–L–Iduronidase in Chinese Hamster Ovary Cells", Protein Expression and Purification, vol. 5, (1994), pp. 225–252.

Ke–Wei Zhao, et al., "Carbohydrate Structures of Recombinant Human α–L–Iduronidase Secreted by Chinese Hamster Ovary Cells", The Journal of Biological Chemistry, vol. 272, No. 36, Issue of Sep. 5, 1997, pp. 22758–22765.

Robin J. Ziegler, et al., "Correction of Enzymatic and Lysosomal Storage Defects In Fabry Mice by Adenovirus–Mediated Gene Transfer", Human Gene Therapy, vol. 10, pp. 1667–1682, (Jul. 1, 1999).

Huaichang Sun, et al., "Retrovirus Vector–Mediated Correction and Cross–Correction of Lysosomal α–Mannosidase Deficiency in Human and Feline Fibroblasts", Human Gene Therapy, vol. 10, pp. 1311–1319, (May 20, 1999).

Ajj Reuser, et al., "Lysosomal storage diseases: cellular pathology, clinical and genetic heterogeneity, therapy", Ann Biol Clin., vol. 52, (1994), pp. 721–728.

Ke–Wei Zhao, et al., "Purification and characterization of human lymphoblast N–acetylglucosamine–1–phosphotransferase", Glycobiology, vol. 2, No. 2, pp. 119–125, 1992.

Takahiro Nagase, et al., "Prediction of the Coding Sequences of Unidentified Human Genes. XV. The Complete Sequences of 100 New(cDNA Clones from Brain Which Code for Large Proteins in vitro", DNA Research, vol. 6, pp. 337–345, 1999.

XP–002226188, "KIAA1208 protein (Fragment)", From Takahiro Nagase, et al., "Prediction of the Coding Sequences of 100 New(cDNA Clones from Brain Which Code for Large Proteins in vitro", DNA Research, vol. 6, pp. 337–345, 1999.

Karen Gheesling Mullis, et al., "Purification and Kinetic Parameters of Bovine Liver N–Acetylglucosamine–1–phosphodiester alpha–N–Acetylglucosaminidase", The Journal of Biological Chemistry, vol. 269, No. 3, Issue of Jan. 21, pp. 1718–1726, 1994.

Jin Kyu Lee, et al., "Purification and Characterization of Human Serum N–Acetylglucosamine–1–phosphodiester alpha–N–Acetylglocosaminidase", Archives of Biochemistry and Biophysics, vol. 319, No. 2. Jun. 1, pp. 413–425, 1995.

Theodore Page, et al., "Purification and characterization of human lymphoblast N–acetylglucosamine–1–phosphodiester alpha–N–acetylglucosaminidase", Glycobiology, vol. 6, No. 6, pp. 619–626, 1996.

Thomas J. Baranski, et al., "Lysosomal Enzyme Phosphorylation", The Journal of Biologial Chemistry, vol. 267, No. 32, Issue of Nov. 15, pp. 23342–23348, 1992.

Ritva Tikkanen, et al., "Several cooperating binding sites mediate the interaction of a lysosomal enzyme with phosphotransferase", The EMBO Journal, vol. 16, No. 22, pp. 6684–6693, 1997.

Fumito Matsuura, et al., "Human alpha–galactosidase A: characterization of the N–linked oligosaccharides on the intracellular and secreted glycoforms overexpressed by Chinese hamster ovary cells", Glycobiology, vol. 8, No. 4, pp. 329–339, 1998.

Shiroh Maguchi, et al., "Elevated Activity and Increased Mannose–6–phosphate in the Carbohydrate Moiety of Cathespin D from Human Hepatoma[1]", Cancer Research, vol. 48, pp. 362–367, Jan. 15, 1988.

Norman W. Barton, et al., "Therapeutic response to intravenous infusions of glucocerebrosidase in a patient with Gaucher disease", Proc. Natl. Acad. Sci, USA, vol. 87, pp. 1913–1916, Mar. 1990.

EXPRESSION OF LYSOSOMAL HYDROLASE IN CELLS EXPRESSING PRO-N-ACETYLGLUCOSAMINE-1-PHOSPHODIESTER α-N-ACETYL GLUCOSIMANIDASE

BACKGROUND OF THE INVENTION

1. Field of the Invention

The present invention provides methods of producing a pro-N-acetylglucosamine-1-phosphodiester α N-acetyl glucosimanidase (phosphodiester α-GlcNAcase), in mammalian cells deficient in the furin proteolytic enzyme and methods of making lysosomal hydrolases having oligosaccharides modified with N-acetylglucosamine-1-phosphate.

2. Discussion of the Background

Lysosomes are organelles in eukaryotic cells that function in the degradation of macromolecules into component parts that can be reused in biosynthetic pathways or discharged by the cell as waste. Normally, these macromolecules are broken down by enzymes known as lysosomal enzymes or lysosomal hydrolases. However, when a lysosomal enzyme is not present in the lysosome or does not function properly, the enzymes specific macromolecular substrate accumulates in the lysosome as "storage material" causing a variety of diseases, collectively known as lysosomal storage diseases.

Lysosomal storage diseases can cause chronic illness and death in hundreds of individuals each year. There are approximately 50 known lysosomal storage diseases, e.g., Pompe Disease, Hurler Syndrome, Fabry Disease, Maroteaux-Lamy Syndrome (mucopolysaccharidosis VI), Morquio Syndrome (mucopolysaccharidosis IV), Hunter Syndrome (mucopolysaccharidosis II), Farber Disease, Acid Lipase Deficiency, Krabbe Disease, and Sly Syndrome (mucopolysaccharidosis VII). In each of these diseases, lysosomes are unable to degrade a specific compound or group of compounds because the enzyme that catalyzes a specific degradation reaction is missing from the lysosome, is present in low concentrations in the lysosome, or is present at sufficient concentrations in the lysosome but is not functioning properly.

Lysosomal Storage diseases have been studied extensively and the enzymes (or lack thereof) responsible for particular diseases have been identified (Scriver, Beaudet, Sly, and Vale, eds., The Metabolic Basis of Inherited Disease, 6th Edition, 1989, Lysosomal Enzymes, Part 11, Chapters 61–72, pp. 1565–1839). Within each disease, the severity and the age at which the disease presents may be a function of the amount of residual lysosomal enzyme that exists in the patient.

The lysosomal targeting pathways have been studied extensively and the process by which lysosomal enzymes are synthesized and transported to the lysosome has been well described. Kornfeld, S. (1986). "Trafficking of lysosomal enzymes in normal and disease states." *Journal of Clinical Investigation* 77: 1–6 and Kornfeld, S. (1990). "Lysosomal enzyme targeting." *Biochem. Soc. Trans.* 18: 367–374. Generally, lysosomal enzymes are synthesized by membrane-bound polysomes in the rough endoplastic reticulum ("RER") along with secretory glycoproteins. In the RER, lysosomal enzymes acquire N-linked oligosaccharides by the en-bloc transfer of a preformed oligosaccharide from dolichol phosphate containing 2 N-acetylglucosamine, 9-mannose and 3-glucose. Glycosylated lysosomal enzymes are then transported to the Golgi apparatus along with secretory proteins. In the cis-Golgi or intermediate compartment lysosomal enzymes are specifically and uniquely modified by the transfer of GlcNAc-phosphate to specific mannoses. In a second step, the GlcNAc is removed thereby exposing the mannose 6-phosphate ("M6P") targeting determinant. The lysosomal enzymes with the exposed M6P binds to M6P receptors in the trans-Golgi and is transported to the endosome and then to the lysosome. In the lysosome, the phosphates are rapidly removed by lysosomal phosphatases and the mannoses are removed by lysosomal mannosidases (Einstein, R. and Gabel, C. A. (1991). "Cell- and ligand-specific dephosphorylation of acid hydrolases: evidence that the mannose 6-phosphate is controlled by compartmentalization." *Journal of Cell Biology* 112: 81–94).

The synthesis of lysosomal enzymes having exposed M6P is catalyzed by two different enzymes, both of which are essential if the synthesis is to occur. The first enzyme is UDP-N-acetylglucosamine: lysosomal enzyme N-Acetylglucosamine-1-phosphotransferase ("GlcNAc-phosphotransferase"). GlcNAc-phosphotransferase catalyzes the transfer of N-acetylglucosamine-1-phosphate from UDP-GlcNAc to the 6 position of 1,2-linked mannoses on the lysosomal enzyme. The recognition and addition of N-acetylgluocosamine-1-phosphate to lysosomal hydrolases by GlcNAc-phosphotransferase is the critical and determining step in lysosomal targeting. The second step is catalyzed by N-acetylglucosamine-1-phosphodiester-N-Acetylglucosaminidase ("phosphodiester α-GlcNAcase"). Phosphodiester α-GlcNAcase catalyzes the removal of N-Acetylglucosamine from the GlcNAc-phosphate modified lysosomal enzyme to generate a terminal M6P on the lysosomal enzyme.

The present inventors have discovered that the phosphodiester α-GlcNAcase comprises a pro-peptide sequence between the signal sequence and the sequence of the active component of the protein sequence. This pro-peptide sequence is proteolytically cleaved to yield a mature active form of phosphodiester α-GlcNAcase. The activity of uncleaved phosphodiester α-GlcNAcase, i.e., containing the pro-peptide sequence was significantly lower than the activity of the phosphodiester α-GlcNAcase when the pro-peptide sequence was cleaved. The inventors have revealed that the pro-peptide sequence contains a recognition site for the site-specific protease Furin and that Furin mediates cleavage of phosphodiester α-GlcNAcase to it's mature form.

SUMMARY OF THE INVENTION

Based on this finding, the invention provides processes of making lysosomal hydrolase in cells which are deficient in Furin and thus have the uncleaved form of phosphodiester α-GlcNAcase. By making the lysosomal hydrolases in these cells, the lysosomal hydrolase is modified with an N-acetylglucosamine-1-phosphate moiety and is not removed, or removed at a low efficiency. After expression and recovery of the lysosomal hydrolase from these Furin deficient cells, the lysosomal hydrolase can be treated with an active form of phosphodiester α-GlcNAcase thereby removing the N-acetylglucosamine moiety to yield a highly phosphorylated lysosomal enzyme, which can be used in enzyme replacement therapies to treat patients suffering from lysosomal storage diseases.

Thus, the method facilitates a simple and reliable method of producing lysosomal hydrolases with the appropriate phospho-modifications thereby reducing the steps necessary to produce a lysosomal hydrolase for therapeutic or experimental use. Additional advantages include that the N-acetylglucosamine-1-phosphate modified oligosaccharides will not bind to trans-Golgi mannose 6-phosphate receptors resulting in secretion of a greater proportion synthesized lysosomal enzyme thereby improving the yield. Additionally, because less lysosomal enzyme is trafficked to the lysosome there should be less processing to mature forms facilitating the preparation of pure precursor lysosomal enzyme preparations. Oligosaccharides not modified by N-acetylglucosamine-1-phosphate should be processed to complex-type oligosaccharides reducing the number of mannose contained in the lysosomal enzyme thereby reducing affinity for mannose receptors.

Accordingly, an object of the present invention is to provide methods of producing lysosomal hydrolases having an Oligosaccharide modified with N-acetylglucosamine-1-phosphateby expressing a nucleotide sequence encoding the lysosomal hydrolase in a mammalian cell that is deficient in the protease Furin.

Another object of the present invention is methods for producing a phosphodiester α-GlcNAcase having its propeptide intact by culturing cells or selecting cells that are furin deficient, where the selection is preferably conducted using Pseudomonas exotoxin A.

BRIEF DESCRIPTION OF THE DRAWINGS

FIG. 1. Western Blot of phosphodiester α-GlcNAcase in the presence or absence of Furin.

FIG. 2. Phosphodiester α-GlcNAcase Activity in the presence or absence of Furin.

FIG. 3. Mannose-6-phosphate binding capacity of β-glucuronidase (β-Gluc) and N-acetyl-β-D-glucosaminidase (NAcGluc). (A) Conditioned media after 24 hours of LoVo culture. (B) Conditioned media after Alkaline Phosphatase treatment. (C) Conditioned media after rh-UCE treatment. (D) Conditioned media after rh-UCE treatment, followed by Alkaline Phosphatase digestion.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausebel et al (eds.), John Wiley & Sons, New York (2001) and the various references cited therein.

"Isolated" means separated out of its natural environment.

"Polynucleotide" in general relates to polyribonucleotides and polydeoxyribonucleotides, it being possible for these to be non-modified RNA or DNA or modified RNA or DNA.

The term "nucleotide sequence" as used herein means a polynucleotide molecule in the form of a separate fragment or as a component of a larger nucleic acid construct that has been derived from DNA or RNA isolated at least once in substantially pure form (i.e., free of contaminating endogenous materials) and in a quantity or concentration enabling identification, manipulation, and recovery of its component nucleotide sequences by standard biochemical methods. Such sequences are preferably provided in the form of an open reading frame uninterrupted by internal non-translated sequences, or introns that are typically present in eukaryotic genes. Sequences of non-translated DNA may be present 5' or 3' from an open reading frame where the same do not interfere with manipulation or expression of the coding region.

The term "nucleic acid molecule" as used herein means RNA or DNA, including cDNA, single or double stranded, and linear or covalently closed molecules. A nucleic acid molecule may also be genomic DNA corresponding to the entire gene or a substantial portion therefor to fragments and derivatives thereof. The nucleotide sequence may correspond to the naturally occurring nucleotide sequence or may contain single or multiple nucleotide substitutions, deletions and/or additions including fragments thereof. All such variations in the nucleic acid molecule retain the ability to encode a biologically active enzyme when expressed in the appropriate host or an enzymatically active fragment thereof. The nucleic acid molecule of the present invention may comprise solely the nucleotide sequence encoding an enzyme or may be part of a larger nucleic acid molecule that extends to the gene for the enzyme. The non-enzyme encoding sequences in a larger nucleic acid molecule may include vector, promoter, terminator, enhancer, replication, signal sequences, or non-coding regions of the gene.

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Other control or regulatory sequences can be employed as is known in the art. Exemplary expression vectors for use in mammalian host cells are well known in the art.

Methods of introducing, transducting or transfecting mammalian cells are well within the knowledge of the skilled artisan. Examples of such methods include calcium phosphate-mediated, liposome-mediated, Dextran-mediated, and electroporation. These and other methods are described in, for example, Sambrook et al (2001) Molecular Cloning: A Laboratory Manual, Cold Spring Harbor Laboratory Press, NY and Current Protocols in Molecular Biology (2001) and Ausebel et al (eds.), John Wiley and Sons, Inc, N.Y.

According to the present invention, the glycoproteins may be produced by the recombinant expression systems described above. The method comprises culturing a host cell transformed with an expression vector comprising a DNA sequence that encodes the glycoprotein under conditions sufficient to promote expression of the glycoprotein.

"Polypeptides" are understood as meaning peptides or proteins which comprise two or more amino acids bonded via peptide bonds.

"Glycoprotein" as used herein means proteins that are endogenously modified to carry one or more carbohydrate moieties on the protein. Within the context of the present invention, lysosomal hydrolase glycoproteins are preferred. Examples of lysosomal hydrolases include α-glucosidase, α-L-iduronidase, α-galactosidase A, arylsulfatase, N-acetylgalactosamine-6-sulfatase or β-galactosidase, iduronate 2-sulfatase, ceramidase, galactocerebrosidase, β-glucuronidase, Heparan N-sulfatase, N-Acetyl-α-glucosaminidase, Acetyl CoA-α-glucosaminide N-acetyl transferase, N-acetyl-glucosamine-6sulfatase, Galactose 6-sulfatase, Arylsulfatase A, B, and C, Arylsulfatase A Cerebroside, Ganglioside, Acid β-galactosidase $G_{M1}$ Galglioside, Acid β-galactosidase, Hexosaminidase A, Hexosaminidase B, α-fucosidase, α-N-Acetyl galactosaminidase, Glycoprotein Neuraminidase, Aspartyl-glucosamine amidase, Acid Lipase, Acid Ceramidase, Lysosomal Sphingomyelinase and other Sphingomyelinases.

The term "biologically active" as used herein means an enzyme or protein having structural, regulatory, or biochemical functions of a naturally occurring molecule.

"Complex carbohydrates" as used herein means contains monosaccharide other than GlnAc and mannose (Kornfeld, R and Kornfeld, S. (1985) Ann Rev Biochem 54:631–664).

In the present invention any mammalian cell can be utilized, primary or established. Preferably, the mammalian cell is an established cell line that proliferates in culture and is amenable to selection as described herein. Examples of such cells include HeLa, 293T, Vero, NIH 3T3, Chinese Hamster Ovary, and NS0.

Mammalian cells can be cultured in dishes, plates, and flasks in the appropriate medium in accordance with standard cell culture protocols (Sambrook et al (2001) Molecular Cloning: A Laboratory Manual, Cold Spring Harbor Laboratory Press, NY and Current Protocols in Molecular Biology (2001) and Ausebel et al (eds.), John Wiley and Sons, Inc, N.Y.). As recognized by the skilled artisan the type of vessel and specific culture conditions will vary depending on the specific cell type, whether the cell is typically cultured in suspension, adherent or in a co-culture with one or more cells.

The GlcNAc-phosphotrasferase is composed of six subunits: 2 α subunits, 2 β-subunits and 2 γ subunits. The amino acid sequence of the a subunit is shown in SEQ ID NO: 4 (amino acids 1–928), the human β subunit is shown in SEQ ID NO: 5 (amino acids 1–328), and the human γ subunit is shown in SEQ ID NO: 7 (amino acids 25–305, signal sequence is in amino acids 1–24).

In another embodiment, the GlcNAc-phosphotransferase is recombinant GlcNAc-phosphotransferase, which has been engineered to remove the membrane binding domain from the polyprotein containing the α/β subunits and the endogenous proteolytic cleavage site is replaced with a non-endogenous site-specific proteolytic cleavage site such as Furin, Factor Xa, Enterokinase, and Genease. After preparing the α/β subunits they can be combined with an isolated γ-subunit to yield a GlcNAc-phosphotransferase enzyme.

The soluble GlcNAc-phosphotransferase protein or polypeptide include the sequences exemplified in this application as well as those which have substantial identity to SEQ ID NO: 2.

The partial rat and Drosphila melanogaster α/β GlcNAc-phosphotransferase amino acid sequences are shown in SEQ ID NO: 14 and 16, respectively.

Preferably, the GlcNAc-phosphotransferase polypeptides are those which are at least 70%, preferably at least 80% and more preferably at least 90% to 95% identical to the GlcNAc-phosphotransferase amino acid sequences described herein.

Polynucleotides which encode the α and β subunits of GlcNAc-phosphotransferase or soluble GlcNAc-phosphotransferase mean the sequences exemplified in this application as well as those which have substantial identity to those sequences and which encode an enzyme having the activity of the α and β subunits of GlcNAc-phosphotransferase. Preferably, such polynucleotides are those which hybridize under stringent conditions and are at least 70%, preferably at least 80% and more preferably at least 90% to 95% identical to those sequences The nucleotide sequence for the human α/β subunit precursor cDNA is shown in SEQ ID NO: 3 (nucleotides 165–3932), the nucleotide sequence of the α subunit is in nucleotides 165–2948 of SEQ ID NO: 3, the nucleotide sequence of the β subunit is shown in nucleotides 2949–3932 of SEQ ID NO: 3, and the nucleotide sequence of the γ subunit is shown in SEQ ID NO: 6 (nucleotides 24–95). The soluble GlcNAc-phosphotransferase nucleotide sequence is shown in SEQ ID NO: 1. The partial rat and Drosphila melanogaster α/β GlcNAc-phosphotransferase nucleotide sequences are shown in SEQ ID NO: 13 and 15, respectively.

Polynucleotides which encode phosphodiester α-GlcNAcase as used herein is understood to mean the sequences exemplified in this application as well as those which have substantial identity to SEQ ID NO: 19 (murine) or SEQ ID NO: 17 (human) and which encode an enzyme having the activity of phosphodiester α-GlcNAcase. Preferably, such polynucleotides are those which hybridize under stringent conditions and are at least 70%, preferably at least 80% and more preferably at least 90% to 95% identical to SEQ ID NOS: 17 and/or 19.

The phosphodiester α-GlcNAcase protein or polypeptide as used herein is understood to mean the sequences exemplified in this application as well as those which have substantial identity to SEQ ID NO: 20 (murine) or SEQ ID NO: 18 (human). Preferably, such polypeptides are those which are at least 70%, preferably at least 80% and more preferably at least 90% to 95% identical to SEQ ID NOS: 18 and/or 20.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60oC. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, Anal. Biochem., 138:267–284 (1984):

$T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with approximately 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The furin deficient cells that are known and available to the skilled artisan may be employed, including but not limited to FD11 cells (Gordon et al (1997) Infection and Immunity 65(8):3370–3375), and those mutant cells described in Moehring and Moehring (1983) Infection and Immunity 41(3):998–1009.

Alternatively, a furin deficient cell may be obtained by exposing cultured cells to mutagenesis treatment, e.g., irradiation, ethidium bromide, bromidated uridine (BrdU) and others, preferably chemical mutagenesis, and more preferred ethyl methane sulfonate mutagenesis, recovering the cells which survive the treatment and selecting for those cells which are found to be resistant to the toxicity of Pseudomonas exotoxin A (see Moebring and Moehrina (1983) Infection and Immunity 41(3):998–1009).

The amount of Pseudomonas exotoxin A can be used as described supra, or can be empirically determined for each individual cell type by titrating various concentration of Pseudomonas exotoxin A on the cells and observing the concentration of Pseudoinonas exotoxin A, which does not result in the killing of all the cells. A preferred range includes 0.5 to 2.0 μg/ml, including 0.75, 1.0, 1.25, 1.5, 1.75, and all values therebetween.

The phrase "highly phosphorylated lysosomal hydrolase" as used herein refers to lysosomal hydrolases which contains more bis-phosphorylated oligosaccharides compared to known naturally occurring or recombinant lysosomal hydrolases. Preferably, the lysosomal hydrolases contains at least 5% bis-phosphorylated oligosaccharides compared to lysosomal hydrolases not treated with the GlcNAc-phosphotransferase described herein. More preferably, the "highly phosphorylated lysosomal hydrolases" has at least 6%, 7%, 8%, 9%, 10%, 11%, 12%, 13%,14%, 15%, 16%, 17%, 18%, 19%, 20%, 21%, 22%,23%, 24%, 25%, 26%, 27%, 28%, 29%,30%, 40%,45%, 50%, 60%, 70%, 80%, 85%, 90%, 95%, 100% bis-phosphorylated oligosaccharides and all values and ranges there between. This highly phosphorylated lysosomal hydrolases have a higher affinity for the M6P receptor and are therefore more efficiently taken into the cell by plasma membrane receptors.

To determine the extent to which the lysosomal hydrolase is phosphorylated, the lysosomal hydrlase pre- and post-phosphorylation treatment can be assayed by binding to Mannose-6-phosphate as described herein and in Hoflack et al (1985) Biochem 260:12008–120014.

When the cells are also furin deficient are employed the resultant lysosomal hydrolases containing the N-acetylglucosamine-1-phosphate is obtained due to the significantly lower phosphodiester-α-GlcNAcase activity. The purified lysosomal hydrolases having a Oligosaccharide modified with N-acetylglucosamine-1-phosphateis then treated in vitro with with phosphodiester α GlcNAcase to remove the N-acetylglucosamine moiety.

In another embodiment of the invention, the cells found to be furin deficient may also be subsequently or previously selected for lectin resistance, preferably ricin resistance as described in Applicants co-pending U.S. applications: "METHOD OF PRODUCING GLYCOPROTEINS HAVING REDUCED COMPLEX CARBOHYDRATES IN MAMMALIAN CELLS" U.S. application Ser. No. 10/023, 890, which was filed Dec. 21, 2001 or METHODS OF PRODUCING HIGH MANNOSE GLYCOPROTEJNS INPLEX CARBOHYDRATE DEFICIENT CELLS", U.S. application Ser. No. 10/023,889, which was filed Dec. 21, 2001 the contents of which are incorporated herein by reference.

Any lysosomal enzyme that uses the M6P transport system can be treated according to the method of the present invention. Examples include α-glucosidase (Fompe Disease), α-L-iduronidase (Hurler Syndrome), α-galactosidase A (Fabry Disease), arylsulfatase (Maroteaux-Lamy Syndrome), N-acetylgalactosamine-6- sulfatase or β-galactosidase (Morquio Syndrome), iduronate 2-sulfatase (Hunter Syndrome), ceramidase (Farber Disease), galactocerebrosidase (Krabbe Disease), β-glucuronidase (Sly Syndrome), Heparan N-sulfatase (Sanfilippo A), N-Acetyl-α-glucosaminidase (Sanfilippo B), Acetyl CoA-α-glucosaminide N-acetyl transferase, N-acetyl-glucosamine-6 sulfatase (Sanfilippo D), Galactose 6-sulfatase (Morquio A), Arylsulfatase A, B, and C (Multiple Sulfatase Deficiency), Arylsulfatase A Cerebroside (Metachromatic Leukodystrophy), Ganglioside sialidase (Mucolipidosis IV), Acid β-galactosidase $G_{MI}$ Galglioside ($G_{MI}$ Gangliosidosis), Acid β-galactosidase (Galactosialidosis), Hexosaminidase A (Tay-Sachs and Variants), Hexosaminidase B (Sandhoff), α-fucosidase (Fuesidosis), α-N-Acetyl galactosaminidase (Schindler Disease), Glycoprotein Neuraminidase (Sialidosis), Aspartyiglucosamine amidase (Aspartylgiucosaminuria), Acid Lipase (Wolman Disease), Acid Ceramidase (Farber Lipogranulomatosis), Lysosomal Sphingomyelinase and other Sphingomyelinase (Nieman-Pick).

Methods for treating any particular lysosomal hydrolase with the GlcNAc-phosphotransferase and phosphodiester α-GlcNAcase are within the knowledge of the skilled artisan. Generally, the lysosomal hydrolase at a concentration of about 10 mg/ml and phosphodiester α-GlcNAcase at a concentration of about 1000 units/mL and the system is allowed to incubate for 2 hours at 37° C. at a pH of about 6–7 and any stabilizers or coenzymes required to facilitate the reaction. The modified lysosomal enzyme having highly phosphorylated oligosaccharides is then recovered by conventional means.

The phosphorylated lysosomal hydrolase can be administered to a patient suffering from the lysosomal storage disorder to replace the deficient hydrolase as appropriate. Thus, the present invention also provides methods for the treatment of lysosomal storage diseases by administering an effective amount of the phosphorylated lysosomal hydrolase of the present invention to a patient diagnosed with the respective disease. As used herein, being diagnosed with a lysosomal storage disorder includes pre-symptomatic phases of the disease and the various symptomatic identifiers associated with the disease. Typically, the pre-symptomatic patient will be diagnosed with the disease by means of a genetic analysis known to the skilled artisan.

While dosages may vary depending on the disease and the patient, phosphorylated hydrolase are generally administered to the patient in amounts of from about 0.1 to about 1000 milligrams per kg of patient per month, preferably from about 1 to about 500 milligrams per kg of patient per month. Amongst various patients the severity and the age at which the disease presents itself may be a function of the amount of residual hydrolase that exists in the patient. As such, the present method of treating lysosomal storage diseases includes providing the phosphorylated lysosomal hydrolase at any or all stages of disease progression.

The hydrolase may be administered by any convenient means, conventionally known to those of ordinary skill in the art. For example, the enzyme may be administered in the form of a pharmaceutical composition containing the enzyme and a pharmaceutically acceptable carrier or by means of a delivery system such as a liposome or a controlled release pharmaceutical composition. The term "pharmaceutically acceptable" refers to molecules and compositions that are physiologically tolerable and do not typically produce an allergic or similar unwanted reaction such as gastric upset or dizziness when administered. Preferably, "pharmaceutically acceptable" means approved by a regulatory agency of the Federal or a state government or listed in the U.S. Pharmacopoeia or other generally recognized pharmacopoeia for use in animals, preferably humans. The term "carrier" refers to a diluent, adjuvant, excipient, or vehicle with which the compound is administered. Such pharmaceutical carriers can be sterile liquids, such as saline solutions, dextrose solutions, glycerol solutions, water and oils emulsions such as those made with oils of petroleum, animal, vegetable, or synthetic origin (peanut oil, soybean oil, mineral oil, or sesame oil). Water, saline solutions, dextrose solutions, and glycerol solutions are preferably employed as carriers, particularly for injectable solutions.

The hydrolase or the composition may be administered by any standard technique compatible with enzymes or their compositions. For example, the enzyme or composition can be administered parenterally, transdermally, or transmucosally, e.g., orally or nasally. Preferably, the hydrolase or composition is administered by intravenous injection.

As described above, the present invention also provides methods of obtaining or producing a phosphodiester α-GlcNAcase from cells deficient in the furin protease. This enzyme can be obtained or produced in the known furin deficient cell lines or in cell lines produced in accordance with the disclosure herein. After the phosphodiester α-GlcNAcase is collected from the cells, it may be stored or immediately cleaved in vitro with a preparation, preferably purified preparation, of the Furin protease. This cleaved phosphodiester α-GlcNAcase can then be used to remove the N-acetylglucosamine-1-phosphate from the lysosomal hydrolases as described herein.

The following Examples provide an illustration of embodiments of the invention and should not be construed to limit the scope of the invention, which is set forth in the appended claims. In the following Examples, all methods described are conventional unless otherwise specified.

EXAMPLES

Differential Specific Activity of CHO and Insect-Expressed Human UCE

CHO K-1 cells were transfected with plasmid pKB6 that encodes an epitope-tagged, soluble human phosphodiester α-GlcNAcase ("Uncovering Enzyme" or UCE). Similarly, insect cells were infected with a baculovirus that contained the epitope-tagged human UCE cDNA (performed by Protein Sciences, Inc.). The UCE-conditioned media from each expression system was affinity-purified via a HPC4 antibody column. The HPC4 eluates were concentrated via Centricons and assayed using the synthetic substrate [$^3$H]GlcNAc-P-Man-α-Me to determine UCE activity. The UCE protein concentration was measured by either absorbance at a wavelength of 280 nm or with a protein quantitation kit e.g., Micro BCA Assay (Pierce-Endogen) and Advanced Protein Assay (Cytoskeleton). The purification of CHO- and insect-expressed UCE is summarized below.

| Sample | Volume (ml) | Protein Conc. (mg/ml) | Total Protein (mg) | UCE Activity (Units/ml) | Total UCE Activity (Units) | Specific Activity (Units/mg) | % yield | Fold Purif. |
|---|---|---|---|---|---|---|---|---|
| CHO-Expressed UCE: | | | | | | | | |
| Conditioned Media | 1400 | 17.4 | 24360 | $8.7 \times 10^3$ | $12.2 \times 10^6$ | 501 | 100 | 1 |
| HPC4 Eluate | 1 | 44.6 | 44.6 | $11 \times 10^6$ | $11.1 \times 10^6$ | $2.5 \times 10^5$ | 91 | 499 |
| Insect-Expressed UCE: | | | | | | | | |
| Conditioned Media | 100 | 15.2 | 1520 | $6 \times 10^3$ | $6 \times 10^5$ | 395 | 100 | 1 |
| HPC4 Eluate | 1 | 0.52 | 0.52 | $2.85 \times 10^5$ | $2.85 \times 10^5$ | $5.5 \times 10^5$ | 48 | 1392 |

Summary of Results:

The CHO-expressed human UCE was efficiently purified via the HPC4 antibody column (91% yield). Approximately 10 mg of UCE was recovered per liter of conditioned CHO media. In contrast, the recovery of the insect-derived UCE was nearly half that of the CHO-derived UCE sample and recovered only 2.5 mg UCE per liter of 96 hr post infected insect media. Interestingly, the specific activity of the insect-derived human UCE was approximately 2-fold higher than the CHO-derived UCE. The major difference between the two UCE species is that the UCE plasmid construct in the insect expression system lacked the UCE pro-sequence.

Protein Sequence of CHO and Insect-Expressed Human UCE

The major difference between the two UCE species is that the UCE plasmid construct in the insect expression system lacked the UCE pro-sequence. Human UCE is a homotetramer and each monomer is synthesized as a pre-pro-UCE that is processed in vivo to generate the mature UCE monomer. The specific activity data show that these two UCE species are functionally distinct. To determine whether a difference is a different translation processing of CHO and insect expressed UCE the following experiments were conducted.

The N-terminal primary amino acid sequence of UCE (amino acids 1–55 of SEQ ID NO: 18) is shown below, the signal peptide is indicated at the N-terminus, the Pro-peptide sequence is underlined and the N-terminal starting amino acids for the mature UCE are shown.

CHO and insect-derived UCE samples were subjected to SDS-PAGE and then transferred to PVDF membrane. The membrane was stained with Ponceau S stain to visualize the protein bands. The insect and UCE bands were excised from the membrane and subjected to N-terminal sequencing. The results are present in the Table below:

N-terminal Sequencing of rh-UCE:

| | CHO-derived UCE: | | | Insect-derived UCE: | | |
|---|---|---|---|---|---|---|
| Cycle # Processed | Amino Acid | % Unprocessed | % Processed | Cycle # | Amino Acid | % |
| 1 | L, D | 69 | 31 | 1 | D | 100 |
| 2 | D | 100 | not detected | 2 | not detected | — |
| 3 | S, T | 60 | 40 | 3 | T | 100 |
| 4 | G | 100 | not detected | 4 | R | 100 |
| 5 | A, V | 68 | 32 | 5 | V | 100 |
| 6 | S | 100 | not detected | 6 | R | 100 |
| 7 | R | 100 | not detected | 7 | A | 100 |
| 8 | D, G | 64 | 36 | 8 | G | 100 |
| 9 | D, N | 55 | 45 | 9 | N | 100 |
| 10 | D | 100 | not detected | 10 | not detected | — |

These results demonstrate that there are major structural differences between the CHO and insect-derived rh-UCE. The CHO-derived UCE is not processed efficiently, i.e., ~65% pro-UCE and 35% mature UCE. In contrast, the insect-derived UCE is 100% mature UCE. The insect UCE was expected to exist only as the mature form because the plasmid lacked a pro-sequence. The data indicate that the majority of the CHO-derived UCE must have either escaped the processing enzyme(s) that converts pro-UCE to the mature UCE or that the processing enzyme(s) responsible for this cleavage is defective in this CHO cell line.

In Vitro Activation of rh-UCE by Furin

The N-terminal amino acid sequencing results of CHO- and insect-derived rh-UCE revealed that there are major structural differences between these two UCE samples. The CHO-derived UCE is not processed efficiently, i.e., ~65% pro-UCE and 35% mature UCE. In contrast, the insect-derived UCE is 100% mature UCE. The data suggests that the most of CHO-derived UCE must have either escaped the processing enzyme(s) that converts pro-UCE to the mature form or that the processing enzyme(s) responsible for this cleavage is defective in this CHO cell line. The human UCE contains a region that lies between pro-sequence and the start of the mature UCE sequence that may serve as a Furin cleavage site based on the primary amino acid sequence (unpublished data, S. Kornfeld & W. Canfield). Furin is a calcium-dependent serine protease that is endogenous to many mammalian cells. This protease requires a minimal furin cleavage site of Arg-X-X-Arg (SEQ ID NO: 22).

The putative furin site in human UCE is

(amino acids 42–52 of SEQ ID NO:18)

To determine whether furin is the enzyme responsible for the post-translational processing of pro-UCE to mature UCE the following experiment was performed.

A time-dependent analysis of UCE in the presence or absence of furin was performed. Twenty micrograms of CHO- and insect-derived UCE were incubated with 20 U furin at 30° C. and 5 μg of each UCE sample as removed after 0, 6, 12, and 24 hours, respectively. Each sample was deglycosylated via PNGaseF and 200 ng of each sample subjected to SDS-PAGE followed by Western blotting using HPC4 mouse 1° antibody and horseradish-conjugated sheep-anti-mouse 2° antibody. All samples were also assayed for UCE activity and graphed as % increase in activity relative to the minus Furin samples.

Figure 2:
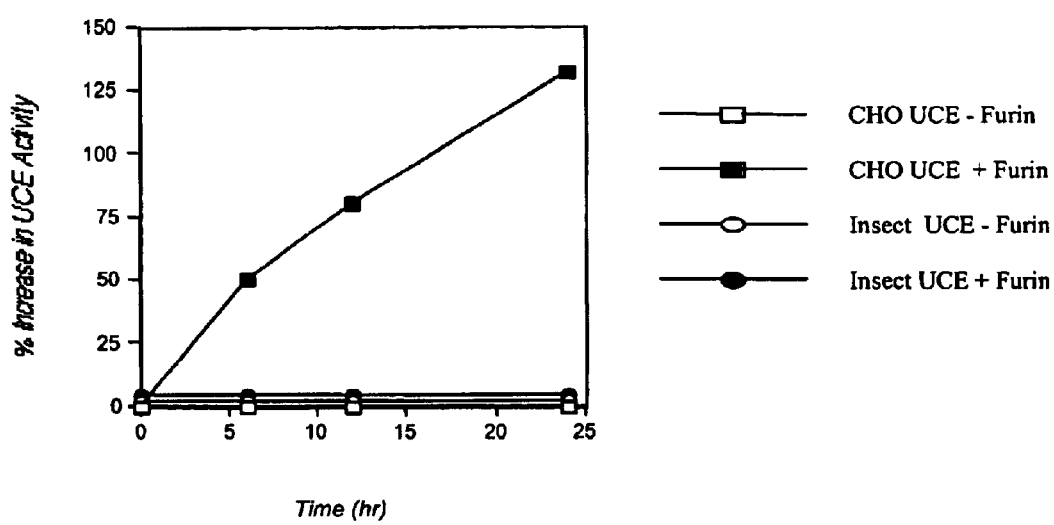

Western blot analysis revealed that the CHO-derived UCE is sensitive to furin cleavage as shown by the progressive conversion of the pro-UCE to the mature form (FIG. 1). The conversion of the pro-UCE to the mature UCE species is furin-dependent because the UCE sample that lacked furin remained as a mixture of pro- and mature UCE forms. In contrast, the insect-derived UCE is not cleaved by furin as shown by the single UCE form. The progressive conversion of the pro-UCE to the mature UCE species was confirmed by the increase in UCE activity (up to 130% increase in activity) relative to the minus furin sample (FIG. 2). The insect-derived UCE did not show any increase in activity because it already exists as the mature form.

Defective Uncovering Enzyme in Furin-Deficient LoVo Cells

LoVo cells are derived from a human colon adenocarcinoma cell line that has shown to be void of furin activity (Lehmann et al (1996) Biochem. J. 317:803–809). The discovery that UCE requires furin for further processing above, prompted further investigation to determine the processing of UCE in furin deficient cells, and thus the UCE obtained.

Figure 3:
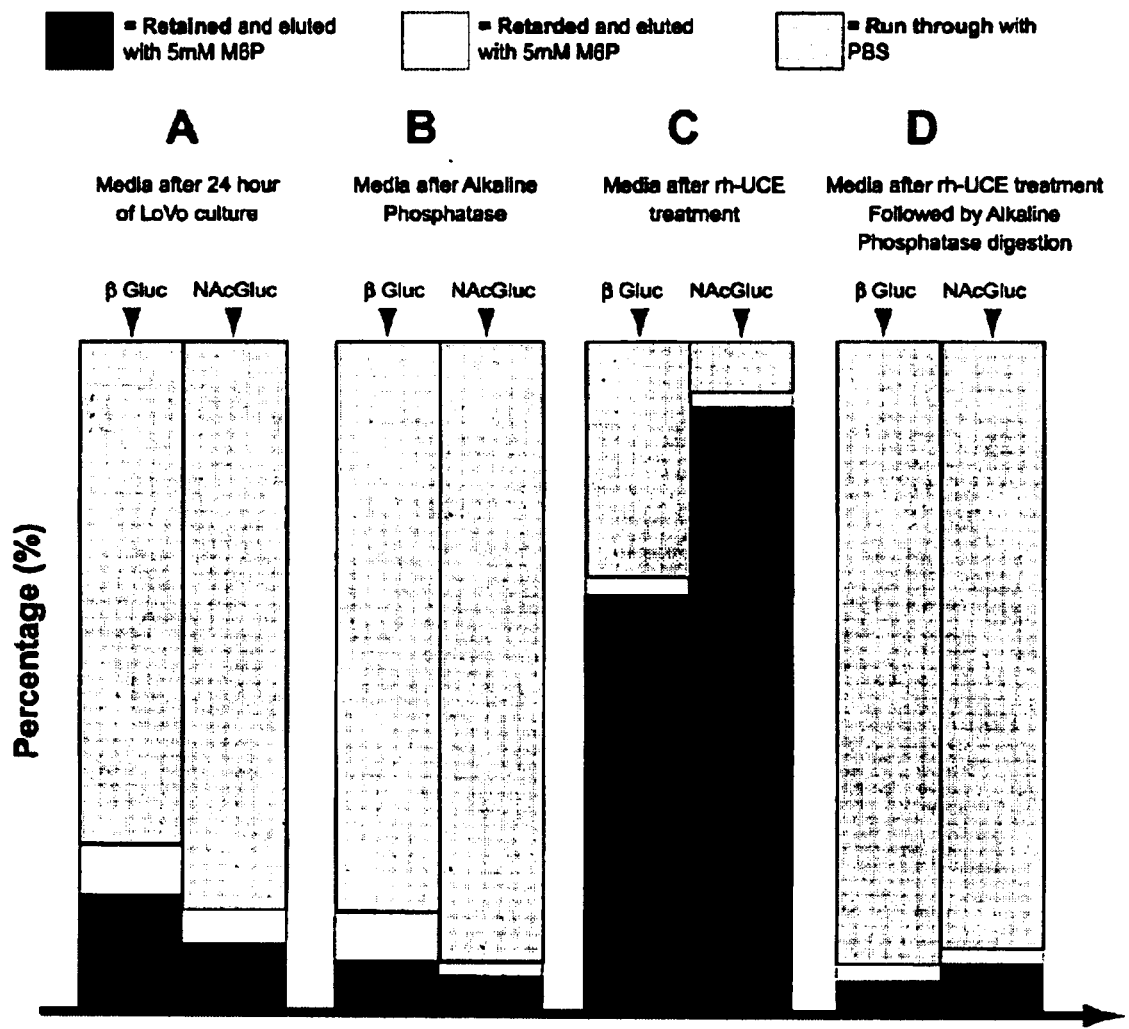

LoVo cells were cultured to confluency and two lysosomal enzymes, β-glucuronidase (β-Gluc) and N-acetyl-β-D-glucosaminidase (NAcGluc) from the conditioned media was assayed for binding on a mannose-6-phosphate receptor column. Sample A was conditioned medium from LoVo cells that was applied to the mannose-6-phosphate receptor column then eluted with 5 mM mannose-6-phosphate. The eluate was subsequently assayed for β-Gluc and NAcGluc activity. Sample B was conditioned medium from LoVo cells and dephosphorylated via alkaline phosphatase prior to mannose-6-phosphate receptor chromatography. Sample C was conditioned medium from LoVo cells that was treated with UCE in vitro prior to mannose-6-phosphate receptor chromatography. Sample D was conditioned medium from LoVo cells that was treated with UCE then alkaline phosphatase prior to mannose-6-phosphate receptor chromatography. The results of this study are shown in FIG. 3.

Obviously, numerous modifications and variations on the present invention are possible in light of the above teachings. It is therefore to be understood that within the scope of the appended claims, the invention may be practiced otherwise than as specifically described herein.

What is claimed is:

1. A method of producing a lysosomal hydrolase having an oligosaccharide modified with N-acetylglucosamine-1-phosphate comprising
   a. contacting a mammalian cell culture expressing a lysosomal hydrolase with a mutagenic agent;
   b. culturing said mammalian cell culture in the presence of Pseudomonas exotoxin A in an amount sufficient to select for cells resistant to the Pseudomonas exotoxin A;
   c. selecting said cells resistant to Pseudomonas exotoxin A; and
   d. isolating said lysosomal hydrolase having an N-acetylglucosamine-1-phosphate from said resistant cells.

2. The method of claim 1, wherein said lysosomal hydrolase is selected from the group consisting of α-glucosidase, α-L-iduronidase, α-galactosidase A, arylsulfatase , N-acetylgalactosamine-6-sulfatase, β-galactosidase, iduronate 2-sulfatase, ceramidase, galactocerebrosidase, β-glucuronidase, Heparan N-sulfatase, N-Acetyl-α-glucosaminidase, Acetyl CoA-α-glucosaminide N-acetyl transferase, N-acetyl-glucosamine-6 sulfatase, Galactose 6-sulfatase, Arylsulfatase A, Arylsulfatase B, Arylsulfatase C, Ganglioside sialidase, Acid β-galactosidase $G_{MI}$ Galglioside, Acid β-galactosidase, Hexosaminidase A, Hexosaminidase B, α-fucosidase, α-N-Acetyl galactosaminidase, Glycoprotein Neuraminidase, Aspartylglucosamine amidase, Acid Lipase, Acid Ceramidase, Lysosomal Sphingomyelinase and Sphingomyelinase.

3. The method of claim 1, further comprising contacting said lysosomal hydrolase having an N-acetylglucosamine- 1-phosphate with an active N-acetylglucosamine-1-phosphodiester α N-acetyl glucosimanidase.

4. The method of claim 3, wherein said N-acetylglucosamine-1-phosphodiester α N-acetyl glucosimanidase comprises amino acids 56 to 515 of SEQ ID NO:18.

5. The method of claim 3, wherein said N-acetylgiucosamine-1-phosphodiester α N-acetyl glucosimanidase is encoded by a nucleotide sequence comprising SEQ ID NO: 17 or a nucleotide sequence that hybridizes under stringent conditions to the complement of SEQ ID NO:17.

6. The method of claim 3, further comprising purifying said lysosomal hydrolase after said contacting.

7. The method of claim 1, wherein said mutagenic agent is a chemical mutagenic agent.

8. The method of claim 7, wherein said mutagenic agent is ethyl methane sulfonate.

9. The method of claim 1, further comprises culturing said mammalian cell culture in the presence of a α 1,2-mannosidase inhibitor.

10. The method of claim 9, wherein said a α 1,2-mannosidase inhibitor comprises both deoxymannojirimyciri and kifunensine.

11. The method of claim 1, further comprising introducing a polynucleotide sequence encoding the lysosomal hydrolase in the cells resistant to Pseudomonas exotoxin A before said isolating said lysosomal hydrolase.

12. The method of claim 11, wherein said lysosomal hydrolase is selected from the group consisting of α-glucosidase, α-L-iduronidase, α-galactosidase A, arylsulfatase, N-acetylgalactosamine-6-sulfatase β-galactosidase, iduronate 2-sulfatase, ceramidase, galactocerebrosidase, β-glucuronidase, Heparan N-sulfatase, N-Acetyl-α-glucosaminidase, Acetyl CoA-αglucosaminide N-acetyl transferase, N-acetyl-glucosamine-6 sulfatase, Galactose 6-sulfatase, Arylsulfatase A, Arylsulfatase B, Arylsulfatase C, Arylsulfatase A Cerebroside, Ganglioside, Acid β-galactosidase $G_{MI}$ Gaiglioside, Acid β-galactosidase, Hexosaminidase A, Hexosaminidase B, α-fucosidase, α-N-Acetyl galactosaminidase, Glycoprotein Neuraminidase, Aspartyiglucosamine amidase, Acid Lipase, Acid Ceramidase, Lysosomal Sphingomyelinase and Sphingomyelinase.

13. The method of claim 11, further comprising contacting said lysosomal hydrolase having an N-acetylglucosamine-1-phosphate with an active N-acetylglucosamine-1-phosphodiester α N-acetyl glucosimanidase.

14. The method of claim 13, wherein said N-acetylglucosamine-1-phosphodiester a N-acetyl glucosimanidase comprises an amino acids 56 to 515 of SEQ ID NO:18.

15. The method of claim 13, wherein said N-acetylglucosatnine-1-phosphodiester a N-acetyl glucosimanidase is encoded by a nucleotide sequence comprising SEQ ID NO: 17 or a nucleotide sequence that hybridizes under stringent conditions to the complement of SEQ ID NO:17.

16. The method of claim 13, further comprising purifying said lysosomal hydrolase after said contacting.

17. The method of claim 11, further comprises culturing said mammalian cell culture in the presence of a a 1,2-mannosidase inhibitor.

18. The method of claim 17, wherein said a a 1,2-mannosidase inhibitor comprises both deoxymannojirimycin and kifunensme.

19. An isolated lysosomal hydrolase produced by the method of claim 1.

20. An isolated lysosomal hydrolase produced by the method of claim 2.

21. An isolated lysosomal hydrolase produced by the method of claim 3.

22. An isolated lysosomal hydrolase produced by the method of claim 4.

23. An isolated lysosomal hydrolase produced by the method of claim 5.

24. An isolated lysosomal hydrolase produced by the method of claim 6.

25. An isolated lysosomal hydrolase produced by the method of claim 7.

26. An isolated lysosomal hydrolase produced by the method of claim 8.

27. An isolated lysosomal hydrolase produced by the method of claim 9.

28. An isolated lysosomal hydrolase produced by the method of claim 10.

29. An isolated lysosomal hydrolase produced by the method of claim 11.

30. An isolated lysosomal hydrolase produced by the method of claim 12.

31. An isolated lysosomal hydrolase produced by the method of claim 13.

32. An isolated lysosomal hydrolase produced by the method of claim 14.

33. An isolated lysosomal hydrolase produced by the method of claim 15.

34. An isolated lysosomal hydrolase produced by the method of claim 16.

35. An isolated lysosomal hydrolase produced by the method of claim 17.

36. An isolated lysosomal hydrolase produced by the method of claim 18.

* * * * *

SEQUENCE LISTING

<160> NUMBER OF SEQ ID NOS: 22

<210> SEQ ID NO 1
<211> LENGTH: 3600
<212> TYPE: DNA
<213> ORGANISM: hybrid

<400> SEQUENCE: 1

```
atggagacag acacactcct gctatgggta ctgctgctct gggttccagg ttccactggt      60
gacgaagatc aggtagatcc gcggttaatc gacggtaagc ttagccgaga tcaataccat     120
gttttgtttg attcctatag agacaatatt gctggaaagt cctttcagaa tcggctttgt     180
ctgcccatgc cgattgacgt tgtttacacc tgggtgaatg gcacagatct tgaactactg     240
aaggaactac agcaggtcag agaacagatg gaggaggagc agaaagcaat gagagaaatc     300
cttgggaaaa acacaacgga acctactaag aagagtgaga agcagttaga gtgtttgcta     360
acacactgca ttaaggtgcc aatgcttgtc ctggacccag ccctgccagc caacatcacc     420
ctgaaggacc tgccatctct ttatccttct tttcattctg ccagtgacat tttcaatgtt     480
gcaaaaccaa aaaaccttc taccaatgtc tcagttgttg tttttgacag tactaaggat     540
gttgaagatg cccactctgg actgcttaaa ggaaatagca gacagacagt atggagggggc     600 tacttgacaa cagataaaga agtccctgga ttagtgctaa tgcaagattt ggctttcctg     660
agtggatttc caccaacatt caaggaaaca aatcaactaa aaacaaaatt gccagaaaat     720
```

```
ctttcctcta aagtcaaact gttgcagttg tattcagagg ccagtgtagc gcttctaaaa    780
ctgaataacc ccaaggattt tcaagaattg aataagcaaa ctaagaagaa catgaccatt    840
gatggaaaag aactgaccat aagtcctgca tatttattat gggatctgag cgccatcagc    900
cagtctaagc aggatgaaga catctctgcc agtcgttttg aagataacga agaactgagg    960
tactcattgc gatctatcga gaggcatgca ccatgggttc ggaatatttt cattgtcacc   1020
aacgggcaga ttccatcctg ctgaaccttg acaatcctcg agtgacaatg agtaacacac   1080
caggatgttt ttcgaaattt gagccacttg cctaccttta gttcacctgc tattgaaagt   1140
cacgttcatc gcatcgaagg gctgtcccag aagtttattt acctaaatga tgatgtcatg   1200
tttgggaagg atgtctggcc agatgatttt tacagtcact ccaaaggcca gaaggtttat   1260
ttgacatggc ctgtgccaaa ctgtgccgag ggctgcccag gttcctggat taaggatggc   1320
tattgtgaca aggcttgtaa taattcagcc tgcgattggg atggtgggga ttgctctgga   1380
aacagtggag ggagtcgcta tattgcagga ggtggaggta ctgggagtat tggagttgga   1440
cagccctggc agtttggtgg aggaataaac agtgtctctt actgtaatca gggatgtgcg   1500
aattcctggc tcgctgataa gttctgtgac caagcatgca atgtcttgtc ctgtgggttt   1560
gatgctggcg actgtgggca agatcatttt catgaattgt ataaagtgat ccttctccca   1620
aaccagactc actatattat tccaaaaggt gaatgcctgc cttatttcag cttttgcaga   1680
gtagccaaaa gaggagttga aggtgcctat agtgacaatc caataattcg acatgcttct   1740
attgccaaca agtggaaaac catccacctc ataatgcaca gtggaatgaa tgccaccaca   1800
atacatttta atctcacgtt tcaaaataca aacgatgaag agttcaaaat gcagataaca   1860
gtggaggtgg acacaaggga gggaccaaaa ctgaattcta cggcccagaa gggttacgaa   1920
aatttagtta gtcccataac acttcttcca gaggcggaaa tccttttga ggatattccc    1980
aaagaaaaac gcttcccgaa gtttaagaga catgatgtta actcaacaag gagagcccag   2040
gaagaggtga aaattcccct ggtaaatatt tcactccttc caaaagacgc ccagttgagt   2100
ctcaatacct tggatttgca actggaacat ggagacatca ctttgaaagg atacaatttg   2160
tccaagtcag ccttgctgag atcatttctg atgaactcac agcatgctaa aataaaaaat   2220
caagctataa taacagatga aacaaatgac agtttggtgg ctccacagga aaacaggtt   2280
cataaaagca tcttgccaaa cagcttagga gtgtctgaaa gattgcagag gttgacttt    2340
cctgcagtga gtgtaaaagt gaatggtcat gaccagggtc agaatccacc cctggacttg   2400
gagaccacag caagatttag agtggaaact cacacccaaa aaaccatagg cggaaatgtg   2460
acaaagaaa agcccccatc tctgattgtt ccactggaaa gccagatgac aaaagaaaag   2520
aaaatcacag ggaaagaaaa agagaacagt agaatggagg aaaatgctga aaatcacata   2580
ggcgttactg aagtgttact tggaagaaag ctgcagcatt acacagatag ttacttgggc   2640
tttttgccat gggagaaaaa aaagtatttc ctagatcttc tcgacgaaga agagtcattg   2700
aagacacaat tggcctactt cactgatagc aagaatagag ccagatacaa gagagataca   2760
tttgcagatt ccctcagata tgtaaataaa attctaaata gcaagtttgg attcacatcg   2820
cggaaagtcc ctgctcacat gcctcacatg attgaccgga ttgttatgca agaactgcaa   2880
gatatgttcc ctgaagaatt tgacaagacg tcatttcaca aagtgcgcca ttctgaggat   2940
atgcagtttg ccttctctta ttttttattat ctcatgagtg cagtgcagcc actgaatata   3000
tctcaagtct tgatgaagt tgatacagat caatctggtg tcttgtctga cagagaaatc    3060
```

-continued

```
cgaacactgg ctaccagaat tcacgaactg ccgttaagtt tgcaggattt gacaggtctg    3120
gaacacatgc taataaattg ctcaaaaatg cttcctgctg atatcacgca gctaaataat    3180
attccaccaa ctcaggaatc ctactatgat cccaacctgc caccggtcac taaaagtcta    3240
gtaacaaact gtaaccagt aactgacaaa atccacaaag catataagga caaaaacaaa    3300
tataggtttg aaatcatggg agaagaagaa atcgctttta aaatgattcg taccaacgtt    3360
tctcatgtgg ttggccagtt ggatgacata agaaaaaacc ctaggaagtt tgtttgcctg    3420
aatgacaaca ttgaccacaa tcataaagat gctcagacag tgaaggctgt tctcagggac    3480
ttctatgaat ccatgttccc catacctttcc caatttgaac tgccaagaga gtatcgaaac    3540
cgtttccttc atatgcatga gctgcaggaa tggagggctt atcgagacaa attgaagtag    3600
```

<210> SEQ ID NO 2
<211> LENGTH: 1199
<212> TYPE: PRT
<213> ORGANISM: hybrid

<400> SEQUENCE: 2

```
Met Glu Thr Asp Thr Leu Leu Leu Trp Val Leu Leu Leu Trp Val Pro
1               5                   10                  15

Gly Ser Thr Gly Asp Glu Asp Gln Val Asp Pro Arg Leu Ile Asp Gly
            20                  25                  30

Lys Leu Ser Arg Asp Gln Tyr His Val Leu Phe Asp Ser Tyr Arg Asp
        35                  40                  45

Asn Ile Ala Gly Lys Ser Phe Gln Asn Arg Leu Cys Leu Pro Met Pro
    50                  55                  60

Ile Asp Val Val Tyr Thr Trp Val Asn Gly Thr Asp Leu Glu Leu Leu
65                  70                  75                  80

Lys Glu Leu Gln Gln Val Arg Glu Gln Met Glu Glu Glu Gln Lys Ala
                85                  90                  95

Met Arg Glu Ile Leu Gly Lys Asn Thr Thr Glu Pro Thr Lys Lys Ser
            100                 105                 110

Glu Lys Gln Leu Glu Cys Leu Leu Thr His Cys Ile Lys Val Pro Met
        115                 120                 125

Leu Val Leu Asp Pro Ala Leu Pro Ala Asn Ile Thr Leu Lys Asp Leu
130                 135                 140

Pro Ser Leu Tyr Pro Ser Phe His Ser Ala Ser Asp Ile Phe Asn Val
145                 150                 155                 160

Ala Lys Pro Lys Asn Pro Ser Thr Asn Val Ser Val Val Phe Asp
                165                 170                 175

Ser Thr Lys Asp Val Glu Asp Ala His Ser Gly Leu Leu Lys Gly Asn
            180                 185                 190

Ser Arg Gln Thr Val Trp Arg Gly Tyr Leu Thr Thr Asp Lys Glu Val
        195                 200                 205

Pro Gly Leu Val Leu Met Gln Asp Leu Ala Phe Leu Ser Gly Phe Pro
    210                 215                 220

Pro Thr Phe Lys Glu Thr Asn Gln Leu Lys Thr Lys Leu Pro Glu Asn
225                 230                 235                 240

Leu Ser Ser Lys Val Lys Leu Leu Gln Leu Tyr Ser Glu Ala Ser Val
                245                 250                 255

Ala Leu Leu Lys Leu Asn Asn Pro Lys Asp Phe Gln Glu Leu Asn Lys
            260                 265                 270

Gln Thr Lys Lys Asn Met Thr Ile Asp Gly Lys Glu Leu Thr Ile Ser
        275                 280                 285
```

```
Pro Ala Tyr Leu Leu Trp Asp Leu Ser Ala Ile Ser Gln Ser Lys Gln
    290                 295                 300
Asp Glu Asp Ile Ser Ala Ser Arg Phe Glu Asp Asn Glu Glu Leu Arg
305                 310                 315                 320
Tyr Ser Leu Arg Ser Ile Glu Arg His Ala Pro Trp Val Arg Asn Ile
                325                 330                 335
Phe Ile Val Thr Asn Gly Gln Ile Pro Ser Trp Leu Asn Leu Asp Asn
            340                 345                 350
Pro Arg Val Thr Ile Val Thr His Gln Asp Val Phe Arg Asn Leu Ser
        355                 360                 365
His Leu Pro Thr Phe Ser Ser Pro Ala Ile Glu Ser His Val His Arg
    370                 375                 380
Ile Glu Gly Leu Ser Gln Lys Phe Ile Tyr Leu Asn Asp Asp Val Met
385                 390                 395                 400
Phe Gly Lys Asp Val Trp Pro Asp Asp Phe Tyr Ser His Ser Lys Gly
                405                 410                 415
Gln Lys Val Tyr Leu Thr Trp Pro Val Pro Asn Cys Ala Glu Gly Cys
            420                 425                 430
Pro Gly Ser Trp Ile Lys Asp Gly Tyr Cys Asp Lys Ala Cys Asn Asn
        435                 440                 445
Ser Ala Cys Asp Trp Asp Gly Gly Asp Cys Ser Gly Asn Ser Gly Gly
    450                 455                 460
Ser Arg Tyr Ile Ala Gly Gly Gly Thr Gly Ser Ile Gly Val Gly
465                 470                 475                 480
Gln Pro Trp Gln Phe Gly Gly Gly Ile Asn Ser Val Ser Tyr Cys Asn
            485                 490                 495
Gln Gly Cys Ala Asn Ser Trp Leu Ala Asp Lys Phe Cys Asp Gln Ala
        500                 505                 510
Cys Asn Val Leu Ser Cys Gly Phe Asp Ala Gly Asp Cys Gly Gln Asp
    515                 520                 525
His Phe His Glu Leu Tyr Lys Val Ile Leu Leu Pro Asn Gln Thr His
    530                 535                 540
Tyr Ile Ile Pro Lys Gly Glu Cys Leu Pro Tyr Phe Ser Phe Ala Glu
545                 550                 555                 560
Val Ala Lys Arg Gly Val Glu Gly Ala Tyr Ser Asp Asn Pro Ile Ile
                565                 570                 575
Arg His Ala Ser Ile Ala Asn Lys Trp Lys Thr Ile His Leu Ile Met
            580                 585                 590
His Ser Gly Met Asn Ala Thr Thr Ile His Phe Asn Leu Thr Phe Gln
        595                 600                 605
Asn Thr Asn Asp Glu Glu Phe Lys Met Gln Ile Thr Val Glu Val Asp
    610                 615                 620
Thr Arg Glu Gly Pro Lys Leu Asn Ser Thr Ala Gln Lys Gly Tyr Glu
625                 630                 635                 640
Asn Leu Val Ser Pro Ile Thr Leu Leu Pro Glu Ala Glu Ile Leu Phe
                645                 650                 655
Glu Asp Ile Pro Lys Glu Lys Arg Phe Pro Lys Phe Lys Arg His Asp
            660                 665                 670
Val Asn Ser Thr Arg Arg Ala Gln Glu Val Lys Ile Pro Leu Val
        675                 680                 685
Asn Ile Ser Leu Leu Pro Lys Asp Ala Gln Leu Ser Leu Asn Thr Leu
    690                 695                 700
```

-continued

```
Asp Leu Gln Leu Glu His Gly Asp Ile Thr Leu Lys Gly Tyr Asn Leu
705                 710                 715                 720

Ser Lys Ser Ala Leu Leu Arg Ser Phe Leu Met Asn Ser Gln His Ala
            725                 730                 735

Lys Ile Lys Asn Gln Ala Ile Ile Thr Asp Glu Thr Asn Asp Ser Leu
        740                 745                 750

Val Ala Pro Gln Glu Lys Gln Val His Lys Ser Ile Leu Pro Asn Ser
    755                 760                 765

Leu Gly Val Ser Glu Arg Leu Gln Arg Leu Thr Phe Pro Ala Val Ser
770                 775                 780

Val Lys Val Asn Gly His Asp Gln Gly Gln Asn Pro Pro Leu Asp Leu
785                 790                 795                 800

Glu Thr Thr Ala Arg Phe Arg Val Glu Thr His Thr Gln Lys Thr Ile
                805                 810                 815

Gly Gly Asn Val Thr Lys Glu Lys Pro Pro Ser Leu Ile Val Pro Leu
            820                 825                 830

Glu Ser Gln Met Thr Lys Glu Lys Lys Ile Thr Gly Lys Glu Lys Glu
        835                 840                 845

Asn Ser Arg Met Glu Glu Asn Ala Glu Asn His Ile Gly Val Thr Glu
    850                 855                 860

Val Leu Leu Gly Arg Lys Leu Gln His Tyr Thr Asp Ser Tyr Leu Gly
865                 870                 875                 880

Phe Leu Pro Trp Glu Lys Lys Lys Tyr Phe Leu Asp Leu Asp Glu
                885                 890                 895

Glu Glu Ser Leu Lys Thr Gln Leu Ala Tyr Phe Thr Asp Ser Lys Asn
            900                 905                 910

Arg Ala Arg Tyr Lys Arg Asp Thr Phe Ala Asp Ser Leu Arg Tyr Val
        915                 920                 925

Asn Lys Ile Leu Asn Ser Lys Phe Gly Phe Thr Ser Arg Lys Val Pro
    930                 935                 940

Ala His Met Pro His Met Ile Asp Arg Ile Val Met Gln Glu Leu Gln
945                 950                 955                 960

Asp Met Phe Pro Glu Glu Phe Asp Lys Thr Ser Phe His Lys Val Arg
                965                 970                 975

His Ser Glu Asp Met Gln Phe Ala Phe Ser Tyr Phe Tyr Leu Met
            980                 985                 990

Ser Ala Val Gln Pro Leu Asn Ile  Ser Gln Val Phe Asp  Glu Val Asp
        995                 1000                1005

Thr Asp  Gln Ser Gly Val Leu  Ser Asp Arg Glu Ile  Arg Thr Leu
    1010                1015                1020

Ala Thr  Arg Ile His Glu Leu  Pro Leu Ser Leu Gln  Asp Leu Thr
    1025                1030                1035

Gly Leu  Glu His Met Leu Ile  Asn Cys Ser Lys Met  Leu Pro Ala
    1040                1045                1050

Asp Ile  Thr Gln Leu Asn Asn  Ile Pro Pro Thr Gln  Glu Ser Tyr
    1055                1060                1065

Tyr Asp  Pro Asn Leu Pro Pro  Val Thr Lys Ser Leu  Val Thr Asn
    1070                1075                1080

Cys Lys  Pro Val Thr Asp Lys  Ile His Lys Ala Tyr  Lys Asp Lys
    1085                1090                1095

Asn Lys  Tyr Arg Phe Glu Ile  Met Gly Glu Glu Glu  Ile Ala Phe
    1100                1105                1110

Lys Met  Ile Arg Thr Asn Val  Ser His Val Val Gly  Gln Leu Asp
```

|  | 1115 |  |  | 1120 |  |  |  | 1125 |  |  |  |

Asp Ile Arg Lys Asn Pro Arg Lys Phe Val Cys Leu Asn Asp Asn
    1130                    1135                  1140

Ile Asp His Asn His Lys Asp Ala Gln Thr Val Lys Ala Val Leu
    1145                    1150                  1155

Arg Asp Phe Tyr Glu Ser Met Phe Pro Ile Pro Ser Gln Phe Glu
    1160                    1165                  1170

Leu Pro Arg Glu Tyr Arg Asn Arg Phe Leu His Met His Glu Leu
    1175                    1180                  1185

Gln Glu Trp Arg Ala Tyr Arg Asp Lys Leu Lys
    1190                    1195

```
<210> SEQ ID NO 3
<211> LENGTH: 5597
<212> TYPE: DNA
<213> ORGANISM: Homo sapiens

<400> SEQUENCE: 3
cggagccgag cgggcgtccg tcgccggagc tgcaatgagc ggcgcccgga ggctgtgacc      60
tgcgcgcggc ggcccgaccg ggcccctga atggcggctc gctgaggcgg cggcggcggc     120
ggcggctcag gctcctcggg gcgtggcgtg gcggtgaagg ggtgatgctg ttcaagctcc     180
tgcagagaca aacctatacc tgcctgtccc acaggtatgg gctctacgtg tgcttcttgg     240
gcgtcgttgt caccatcgtc tccgccttcc agttcggaga ggtggttctg aatggagcc      300 gagatcaata ccatgttttg tttgattcct atagagacaa tattgctgga aagtcctttc     360
agaatcggct ttgtctgccc atgccgattg acgttgttta cacctgggtg aatggcacag     420
atcttgaact actgaaggaa ctacagcagg tcagagaaca gatggaggag gagcagaaag     480
caatgagaga aatccttggg aaaaacacaa cggaacctac taagaagagt gagaagcagt     540
tagagtgttt gctaacacac tgcattaagg tgccaatgct tgtactggac ccagccctgc     600
cagccaacat caccctgaag gacgtgccat ctctttatcc ttcttttcat tctgccagtg     660
acattttcaa tgttgcaaaa ccaaaaaacc cttctaccaa tgtctcagtt gttgtttttg     720
acagtactaa ggatgttgaa gatgcccact ctggactgct taaggaaat agcagacaga     780 cagtatggag ggggtacttg acaacagata agaagtccc tggattagtg ctaatgcaag     840
atttggcttt cctgagtgga tttccaccaa cattcaagga acaaatcaa ctaaaaacaa     900 aattgccaga aaatctttcc tctaaagtca aactgttgca gttgtattca gaggccagtg     960
tagcgcttct aaaactgaat aaccccaagg attttcaaga attgaataag caaactaaga    1020
agaacatgac cattgatgga aaagaactga ccataagtcc tgcatattta ttatgggatc    1080
tgagcgccat cagccagtct aagcaggatg aagacatctc tgccagtcgt tttgaagata    1140
acgaagaact gaggtactca ttgcgatcta tcgagaggca tgcaccatgg gttcggaata    1200 tttttcattgt caccaacggg cagattccat cctggctgaa ccttgacaat cctcgagtga    1260
caatagtaac acaccaggat gttttttcgaa atttgagcca cttgcctacc tttagttcac    1320
ctgctattga aagtcacatt catcgcatcg aagggctgtc ccagaagttt atttacctaa    1380
atgatgatgt catgtttggg aaggatgtct ggcagatga ttttttacagt cactccaaag    1440 gccagaaggt ttatttgaca tggcctgtgc caaactgtgc cgagggctgc ccaggttcct    1500
ggattaagga tggctattgt gacaaggctt gtaataattc agcctgcgat tgggatggtg    1560 ggattgctc tggaaacagt ggagggagtc gctatattgc aggaggtgga ggtactggga    1620
```

```
gtattggagt tggacacccc tggcagtttg gtggaggaat aaacagtgtc tcttactgta    1680
atcagggatg tgcgaattcc tggctcgctg ataagttctg tgaccaagca tgcaatgtct    1740
tgtcctgtgg gtttgatgct ggcgactgtg ggcaagatca ttttcatgaa ttgtataaag    1800
tgatccttct cccaaaccag actcactata ttattccaaa aggtgaatgc ctgccttatt    1860
tcagctttgc agaagtagcc aaaagaggag ttgaaggtgc ctatagtgac aatccaataa    1920
ttcgacatgc ttctattgcc aacaagtgga aaaccatcca cctcataatg cacagtggaa    1980
tgaatgccac cacaatacat tttaatctca cgtttcaaaa tacaaacgat gaagagttca    2040
aaatgcagat aacagtggag gtggacacaa gggagggacc aaaactgaat tctacggccc    2100
agaagggtta cgaaaattta gttagtccca taacacttct tccagaggcg aaatcctttt    2160
ttgaggatat tcccaaagaa aaacgcttcc gaagtttaa gagacatgat gttaactcaa     2220
caaggagagc ccaggaagag gtgaaaattc ccctggtaaa tatttcactc cttccaaaag    2280
acgcccagtt gagtctcaat accttggatt gcaactggaa acatgagaca tcactttga    2340 aaggatacaa tttgtccaag tcagccttgc tgagatcatt tctgatgaac tcacagcatg    2400
ctaaaataaa aaatcaagct ataataacag atgaaacaaa tgcacagttg gtggctccac    2460
aggaaaaaca ggttcataaa agcatcttgc caaacagctt aggagtgtct gaaagattgc    2520
agaggttgac ttttcctgca gtgagtgtaa agtgaatgg tcatgaccag ggtcagaatc     2580 caccctgga cttggagacc acagcaagat ttagagtgga aactcacacc caaaaaacca    2640
taggcggaaa tgtgacaaaa gaaaagcccc catctctgat tgttccactg aaagccagat   2700
tgacaaaaga aagaaaatc acagggaaag aaaaagagaa cagtagaatg gaggaaaatg   2760
ctgaaaatca cataggcgtt actgaagtgt tacttggaag aaagctgcag cattacacag    2820
atagttactt gggcttttg ccatgggaga aaaaaagta ttcccaagat cttctcgacg      2880
aagaagagtc attgaagaca caattggcat acttcactga tagcaaaaat actgggaggc    2940
aactaaaaga tacatttgca gattccctca gatatgtaaa taaaattcta aatagcaagt    3000
ttggattcac atcgcggaaa gtccctgctc acatgcctca catgattgac cggattgtta    3060
tgcaagaact gcaagatatg ttccctgaag aatttgacaa gacgtcattt cacaaagtgc    3120
gccattctga ggatatgcag tttgccttct cttattttta ttatctcatg agtgcagtgc    3180
agccactgaa tatatctcaa gtctttgatg aagttgatac agatcaatct ggtgtcttgt    3240
ctgacagaga aatccgaaca ctggctacca gaattcacga actgccgtta agtttgcagg    3300
atttgacagg tctggaacac atgctaataa attgctcaaa aatgcttcct gctgatatca    3360
cgcagctaaa taatattcca ccaactcagg aatcctacta tgatcccaac ctgccaccgg    3420
tcactaaaag tctagtaaca aactgtaaac cagtaactga caaaatccac aaagcatata    3480
aggacaaaaa caaatatagg tttgaaatca tgggagaaga agaaatcgct tttaaaatga    3540
ttcgtaccaa cgtttctcat gtggttggcc agttggatga cataagaaaa accctagga    3600 agtttgtttg cctgaatgac aacattgacc acaatcataa agatgctcag acagtgaagg    3660
ctgttctcag ggacttctat gaatccatgt tccccatacc ttcccaattt gaactgccaa    3720
gagagtatcg aaaccgtttc cttcatatgc atgagctgca ggaatggagg cttatcgag    3780 acaaattgaa gttttggacc cattgtgtac tagcaacatt gattatgttt actatattct    3840
cattttttgc tgagcagtta attgcactta agcggaagat atttcccaga aggaggatac    3900
acaaagaagc tagtcccaat cgaatcagag tatagaagat cttcatttga aaaccatcta    3960
cctcagcatt tactgagcat tttaaaactc agcttcacag agatgtcttt gtgatgtgat    4020
```

```
gcttagcagt ttggcccgaa gaaggaaaat atccagtacc atgctgtttt gtggcatgaa    4080
tatagcccac tgactaggaa ttatttaacc aacccactga aaacttgtgt gtcgagcagc    4140
tctgaactga ttttactttt aaagaatttg ctcatggacc tgtcatcctt tttataaaaa    4200
ggctcactga caagagacag ctgttaattt cccacagcaa tcattgcaga ctaactttat    4260
taggagaagc ctatgccagc tgggagtgat tgctaagagg ctccagtctt tgcattccaa    4320
agccttttgc taaagttttg cactttttt ttttcatttc ccattttaa gtagttacta    4380 agttaactag ttattcttgc ttctgagtat aacgaattgg gatgtctaaa cctattttta    4440
tagatgttat ttaaataatg cagcaatatc acctcttatt gacaatacct aaattatgag    4500
ttttattaat atttaagact gtaaatggtc ttaaaccact aactactgaa gagctcaatg    4560
attgacatct gaaatgcttt gtaattattg acttcagccc ctaagaatgc tatgatttca    4620
cgtgcaggtc taatttcaac aggctagagt tagtactact taccagatgt aattatgttt    4680
tggaaatgta catattcaaa cagaagtgcc tcatttaga aatgagtagt gctgatggca    4740
ctggcacatt acagtggtgt cttgtttaat actcattggt atattccagt agctatctct    4800
ctcagttggt ttttgataga acagaggcca gcaaactttc tttgtaaaag gctggttagt    4860
aaattattgc aggccacctg tgtctttgtc atacattctt cttgctgttg tttagtttgt    4920 ttttttcaa acaaccctct aaaaatgtaa aaccatgtt tagcttgcag ctgtacaaaa    4980
actgcccacc agccagatgt gaccctcagg ccatcatttg ccaatcactg agaattattt    5040
ttgttgttgt tgttgttgtt gttttgaga cagagtctct ctctgttgcc caggctggag    5100
tgcagtggcg caatctcagc tcactgcaac ctccgcctcc cgggttcaag cagttctgtc    5160
tcagccttct gagtagctgg gactacaggt gcatgccacc acaccctgct aattttgta    5220 tttttagtag agacgggggt tccaccatat tggtcaggct tatcttgaac tcctgacctc    5280
aggtgatcca cctgcctctg cctcccaaag tgctgagatt acaggcataa gccagtgcac    5340
ccagccgaga attagtattt ttatgtatgg ttaaaccttg gcgtctagcc atattttatg    5400
tcataataca atggatttgt gaagagcaga ttccatgagt aactctgaca ggtatttag    5460 atcatgatct caacaatatt cctcccaaat ggcatacatc ttttgtacaa agaacttgaa    5520
atgtaaatac tgtgtttgtg ctgtaagagt tgtgtatttc aaaaactgaa atctcataaa    5580
aagttaaatt ttgaaaa                                                    5597
```

<210> SEQ ID NO 4
<211> LENGTH: 928
<212> TYPE: PRT
<213> ORGANISM: Homo sapiens

<400> SEQUENCE: 4

```
Met Leu Phe Lys Leu Leu Gln Arg Gln Thr Tyr Thr Cys Leu Ser His
1               5                   10                  15

Arg Tyr Gly Leu Tyr Val Cys Phe Leu Gly Val Val Thr Ile Val
            20                  25                  30

Ser Ala Phe Gln Phe Gly Glu Val Leu Glu Trp Ser Arg Asp Gln
        35                  40                  45

Tyr His Val Leu Phe Asp Ser Tyr Arg Asp Asn Ile Ala Gly Lys Ser
    50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
```

-continued

```
                85                  90                  95
Arg Glu Gln Met Glu Glu Gln Lys Ala Met Arg Glu Ile Leu Gly
                100                 105                 110
Lys Asn Thr Thr Glu Pro Thr Lys Lys Ser Glu Lys Gln Leu Glu Cys
                115                 120                 125
Leu Leu Thr His Cys Ile Lys Val Pro Met Leu Val Leu Asp Pro Ala
145             130                 135                 140
Leu Pro Ala Asn Ile Thr Leu Lys Asp Val Pro Ser Leu Tyr Pro Ser
145             150                 155                 160
Phe His Ser Ala Ser Asp Ile Phe Asn Val Ala Lys Pro Lys Asn Pro
                165                 170                 175
Ser Thr Asn Val Ser Val Val Val Phe Asp Ser Thr Lys Asp Val Glu
                180                 185                 190
Asp Ala His Ser Gly Leu Leu Lys Gly Asn Ser Arg Gln Thr Val Trp
                195                 200                 205
Arg Gly Tyr Leu Thr Thr Asp Lys Glu Val Pro Gly Leu Val Leu Met
                210                 215                 220
Gln Asp Leu Ala Phe Leu Ser Gly Phe Pro Pro Thr Phe Lys Glu Thr
225             230                 235                 240
Asn Gln Leu Lys Thr Lys Leu Pro Glu Asn Leu Ser Ser Lys Val Lys
                245                 250                 255
Leu Leu Gln Leu Tyr Ser Glu Ala Ser Val Ala Leu Leu Lys Leu Asn
                260                 265                 270
Asn Pro Lys Asp Phe Gln Glu Leu Asn Lys Gln Thr Lys Lys Asn Met
                275                 280                 285
Thr Ile Asp Gly Lys Glu Leu Thr Ile Ser Pro Ala Tyr Leu Leu Trp
                290                 295                 300
Asp Leu Ser Ala Ile Ser Gln Ser Lys Gln Asp Glu Asp Ile Ser Ala
305             310                 315                 320
Ser Arg Phe Glu Asp Asn Glu Glu Leu Arg Tyr Ser Leu Arg Ser Ile
                325                 330                 335
Glu Arg His Ala Pro Trp Val Arg Asn Ile Phe Ile Val Thr Asn Gly
                340                 345                 350
Gln Ile Pro Ser Trp Leu Asn Leu Asp Asn Pro Arg Val Thr Ile Val
                355                 360                 365
Thr His Gln Asp Val Phe Arg Asn Leu Ser His Leu Pro Thr Phe Ser
                370                 375                 380
Ser Pro Ala Ile Glu Ser His Ile His Arg Ile Glu Gly Leu Ser Gln
385             390                 395                 400
Lys Phe Ile Tyr Leu Asn Asp Asp Val Met Phe Gly Lys Asp Val Trp
                405                 410                 415
Pro Asp Asp Phe Tyr Ser His Ser Lys Gly Gln Lys Val Tyr Leu Thr
                420                 425                 430
Trp Pro Val Pro Asn Cys Ala Glu Gly Cys Pro Gly Ser Trp Ile Lys
                435                 440                 445
Asp Gly Tyr Cys Asp Lys Ala Cys Asn Ser Ala Cys Asp Trp Asp
450             455                 460
Gly Gly Asp Cys Ser Gly Asn Ser Gly Gly Ser Arg Tyr Ile Ala Gly
465             470                 475                 480
Gly Gly Gly Thr Gly Ser Ile Gly Val Gly His Pro Trp Gln Phe Gly
                485                 490                 495
Gly Gly Ile Asn Ser Val Ser Tyr Cys Asn Gln Gly Cys Ala Asn Ser
                500                 505                 510
```

-continued

Trp Leu Ala Asp Lys Phe Cys Asp Gln Ala Cys Asn Val Leu Ser Cys
    515                 520                 525

Gly Phe Asp Ala Gly Asp Cys Gly Gln Asp His Phe His Glu Leu Tyr
    530                 535                 540

Lys Val Ile Leu Leu Pro Asn Gln Thr His Tyr Ile Ile Pro Lys Gly
545                 550                 555                 560

Glu Cys Leu Pro Tyr Phe Ser Phe Ala Glu Val Ala Lys Arg Gly Val
                565                 570                 575

Glu Gly Ala Tyr Ser Asp Asn Pro Ile Ile Arg His Ala Ser Ile Ala
            580                 585                 590

Asn Lys Trp Lys Thr Ile His Leu Ile Met His Ser Gly Met Asn Ala
        595                 600                 605

Thr Thr Ile His Phe Asn Leu Thr Phe Gln Asn Thr Asn Asp Glu Glu
    610                 615                 620

Phe Lys Met Gln Ile Thr Val Glu Val Asp Thr Arg Glu Gly Pro Lys
625                 630                 635                 640

Leu Asn Ser Thr Ala Gln Lys Gly Tyr Glu Asn Leu Val Ser Pro Ile
                645                 650                 655

Thr Leu Leu Pro Glu Ala Glu Ile Leu Phe Glu Asp Ile Pro Lys Glu
            660                 665                 670

Lys Arg Phe Pro Lys Phe Arg His Asp Val Asn Ser Thr Arg Arg
        675                 680                 685

Ala Gln Glu Glu Val Lys Ile Pro Leu Val Asn Ile Ser Leu Leu Pro
    690                 695                 700

Lys Asp Ala Gln Leu Ser Leu Asn Thr Leu Asp Leu Gln Leu Glu His
705                 710                 715                 720

Gly Asp Ile Thr Leu Lys Gly Tyr Asn Leu Ser Lys Ser Ala Leu Leu
                725                 730                 735

Arg Ser Phe Leu Met Asn Ser Gln His Ala Lys Ile Lys Asn Gln Ala
            740                 745                 750

Ile Ile Thr Asp Glu Thr Asn Asp Ser Leu Val Ala Pro Gln Glu Lys
        755                 760                 765

Gln Val His Lys Ser Ile Leu Pro Asn Ser Leu Gly Val Ser Glu Arg
    770                 775                 780

Leu Gln Arg Leu Thr Phe Pro Ala Val Ser Val Lys Val Asn Gly His
785                 790                 795                 800

Asp Gln Gly Gln Asn Pro Pro Leu Asp Leu Glu Thr Thr Ala Arg Phe
                805                 810                 815

Arg Val Glu Thr His Thr Gln Lys Thr Ile Gly Gly Asn Val Thr Lys
            820                 825                 830

Glu Lys Pro Pro Ser Leu Ile Val Pro Leu Glu Ser Gln Met Thr Lys
        835                 840                 845

Glu Lys Lys Ile Thr Gly Lys Glu Lys Glu Asn Ser Arg Met Glu Glu
    850                 855                 860

Asn Ala Glu Asn His Ile Gly Val Thr Glu Val Leu Leu Gly Arg Lys
865                 870                 875                 880

Leu Gln His Tyr Thr Asp Ser Tyr Leu Gly Phe Leu Pro Trp Glu Lys
                885                 890                 895

Lys Lys Tyr Phe Gln Asp Leu Leu Asp Glu Glu Glu Ser Leu Lys Thr
            900                 905                 910

Gln Leu Ala Tyr Phe Thr Asp Ser Lys Asn Thr Gly Arg Gln Leu Lys
        915                 920                 925

<210> SEQ ID NO 5
<211> LENGTH: 328
<212> TYPE: PRT
<213> ORGANISM: Homo sapiens

<400> SEQUENCE: 5

```
Asp Thr Phe Ala Asp Ser Leu Arg Tyr Val Asn Lys Ile Leu Asn Ser
1               5                   10                  15

Lys Phe Gly Phe Thr Ser Arg Lys Val Pro Ala His Met Pro His Met
            20                  25                  30

Ile Asp Arg Ile Val Met Gln Glu Leu Gln Asp Met Phe Pro Glu Glu
        35                  40                  45

Phe Asp Lys Thr Ser Phe His Lys Val Arg His Ser Glu Asp Met Gln
    50                  55                  60

Phe Ala Phe Ser Tyr Phe Tyr Tyr Leu Met Ser Ala Val Gln Pro Leu
65                  70                  75                  80

Asn Ile Ser Gln Val Phe Asp Glu Val Asp Thr Asp Gln Ser Gly Val
                85                  90                  95

Leu Ser Asp Arg Glu Ile Arg Thr Leu Ala Thr Arg Ile His Glu Leu
            100                 105                 110

Pro Leu Ser Leu Gln Asp Leu Thr Gly Leu Glu His Met Leu Ile Asn
        115                 120                 125

Cys Ser Lys Met Leu Pro Ala Asp Ile Thr Gln Leu Asn Asn Ile Pro
    130                 135                 140

Pro Thr Gln Glu Ser Tyr Tyr Asp Pro Asn Leu Pro Pro Val Thr Lys
145                 150                 155                 160

Ser Leu Val Thr Asn Cys Lys Pro Val Thr Asp Lys Ile His Lys Ala
                165                 170                 175

Tyr Lys Asp Lys Asn Lys Tyr Arg Phe Glu Ile Met Gly Glu Glu Glu
            180                 185                 190

Ile Ala Phe Lys Met Ile Arg Thr Asn Val Ser His Val Val Gly Gln
        195                 200                 205

Leu Asp Asp Ile Arg Lys Asn Pro Arg Lys Phe Val Cys Leu Asn Asp
    210                 215                 220

Asn Ile Asp His Asn His Lys Asp Ala Gln Thr Val Lys Ala Val Leu
225                 230                 235                 240

Arg Asp Phe Tyr Glu Ser Met Phe Pro Ile Pro Ser Gln Phe Glu Leu
                245                 250                 255

Pro Arg Glu Tyr Arg Asn Arg Phe Leu His Met His Glu Leu Gln Glu
            260                 265                 270

Trp Arg Ala Tyr Arg Asp Lys Leu Lys Phe Trp Thr His Cys Val Leu
        275                 280                 285

Ala Thr Leu Ile Met Phe Thr Ile Phe Ser Phe Phe Ala Glu Gln Leu
    290                 295                 300

Ile Ala Leu Lys Arg Lys Ile Phe Pro Arg Arg Ile His Lys Glu
305                 310                 315                 320

Ala Ser Pro Asn Arg Ile Arg Val
                325
```

<210> SEQ ID NO 6
<211> LENGTH: 1219
<212> TYPE: DNA
<213> ORGANISM: Homo sapiens

<400> SEQUENCE: 6

-continued

```
gtagagcgca ggtgcgcggc tcgatggcgg cggggctggc gcggctcctg ttgctcctcg      60
ggctctcggc cggcgggccc gcgccggcag gtgcagcgaa gatgaaggtg gtggaggagc     120
ccaacgcgtt tggggtgaac aacccgttct tgcctcaggc cagtcgcctc caggccaaga     180
gggatccttc acccgtgtct ggacccgtgc atctcttccg actctcgggc aagtgcttca     240
gcctggtgga gtccacgtac aagtatgagt tctgcccgtt ccacaacgtg acccagcacg     300
agcagacctt ccgctggaac gcctacagtg ggatcctcgg catctggcac gagtgggaga     360
tcgccaacaa caccttcacg ggcatgtgga tgagggacgg tgacgcctgc cgttcccgga     420
gccggcagag caaggtggag ctggcgtgtg gaaaaagcaa ccggctggcc catgtgtccg     480
agccgagcac ctgcgtctat gcgctgacgt cgagaccccc ctcgtctgc caccccacg      540
ccttgctagt gtacccaacc ctgccagagg ccctgcagcg cagtgggac caggtagagc      600
aggacctggc cgatgagctg atcaccccccc agggccatga agttgctg aggacacttt      660
ttgaggatgc tggctactta agaccccag aagaaaatga acccacccag ctggagggag      720
gtcctgacag cttgggttt gagaccctgg aaaactgcag gaaggctcat aaagaactct      780
caaaggagat caaaggctg aaaggtttgc tcacccagca cggcatcccc tacacgaggc      840
ccacagaaac ttccaacttg gagcacttgg gccacgagac gcccagagcc aagtctccag      900
agcagctgcg gggtgaccca ggactgcgtg ggagtttgtg accttgtggt gggagagcag      960
aggtggacgc ggccgagagc cctacagaga agctggctgg taggacccgc aggaccagct     1020
gaccaggctt gtgctcagag aagcagacaa aacaaagatt caaggtttta attaattccc     1080
atactgataa aaataactcc atgaattctg taaaccattg cataaatgct atagtgtaaa     1140
aaaatttaaa caagtgttaa ctttaaacag ttcgctacaa gtaaatgatt ataaatacta     1200
aaaaaaaaaa aaaaaaaaa                                                  1219
```

<210> SEQ ID NO 7
<211> LENGTH: 305
<212> TYPE: PRT
<213> ORGANISM: Homo sapiens

<400> SEQUENCE: 7

```
Met Ala Ala Gly Leu Ala Arg Leu Leu Leu Leu Gly Leu Ser Ala
1               5                   10                  15

Gly Gly Pro Ala Pro Ala Gly Ala Ala Lys Met Lys Val Val Glu Glu
            20                  25                  30

Pro Asn Ala Phe Gly Val Asn Asn Pro Phe Leu Pro Gln Ala Ser Arg
        35                  40                  45

Leu Gln Ala Lys Arg Asp Pro Ser Pro Val Ser Gly Pro Val His Leu
    50                  55                  60

Phe Arg Leu Ser Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
            100                 105                 110

Ile Ala Asn Asn Thr Phe Thr Gly Met Trp Met Arg Asp Gly Asp Ala
        115                 120                 125

Cys Arg Ser Arg Ser Arg Gln Ser Lys Val Glu Leu Ala Cys Gly Lys
    130                 135                 140

Ser Asn Arg Leu Ala His Val Ser Glu Pro Ser Thr Cys Val Tyr Ala
145                 150                 155                 160
```

```
Leu Thr Phe Glu Thr Pro Leu Val Cys His Pro His Ala Leu Leu Val
                165                 170                 175

Tyr Pro Thr Leu Pro Glu Ala Leu Gln Arg Gln Trp Asp Gln Val Glu
            180                 185                 190

Gln Asp Leu Ala Asp Glu Leu Ile Thr Pro Gln Gly His Glu Lys Leu
            195                 200                 205

Leu Arg Thr Leu Phe Glu Asp Ala Gly Tyr Leu Lys Thr Pro Glu Glu
        210                 215                 220

Asn Glu Pro Thr Gln Leu Glu Gly Gly Pro Asp Ser Leu Gly Phe Glu
225                 230                 235                 240

Thr Leu Glu Asn Cys Arg Lys Ala His Lys Glu Leu Ser Lys Glu Ile
                245                 250                 255

Lys Arg Leu Lys Gly Leu Leu Thr Gln His Gly Ile Pro Tyr Thr Arg
            260                 265                 270

Pro Thr Glu Thr Ser Asn Leu Glu His Leu Gly His Glu Thr Pro Arg
        275                 280                 285

Ala Lys Ser Pro Glu Gln Leu Arg Gly Asp Pro Gly Leu Arg Gly Ser
    290                 295                 300

Leu
305

<210> SEQ ID NO 8
<211> LENGTH: 5229
<212> TYPE: DNA
<213> ORGANISM: Mus musculus

<400> SEQUENCE: 8
ggcggtgaag gggtgatgct gttcaagctc ctgcagagac agacctatac ctgcctatcc      60
cacaggtatg ggctctacgt ctgcttcgtg ggcgtcgttg tcaccatcgt ctcggctttc     120
cagttcggag aggtggttct ggaatggagc cgagatcagt accatgtttt gtttgattcc     180
tacagagaca acattgctgg gaaatccttt cagaatcggc tctgtctgcc catgccaatc     240
gacgtggttt acacctgggt gaatggcact gaccttgaac tgctaaagga gctacagcag     300
gtccgagagc acatggagga gagcagaga gccatgcggg aaaccctcgg gaagaacaca     360
accgaaccga caagaagag tgagaagcag ctggaatgtc tgctgacgca ctgcattaag     420
gtgcccatgc ttgttctgga cccggccctg ccagccacca tcaccctgaa ggatctgcca     480 acccttacc catctttcca cgcgtccagc gacatgttca atgttgcgaa accaaaaaat     540
ccgtctacaa atgtccccgt tgtcgttttt gacactacta aggatgttga agacgcccat     600
gctggaccgt ttaagggagg ccagcaaaca gatgtttgga gagcctactt gacaacagac     660
aaagacgccc ctggcttagt gctgatacaa ggcttggcgt tcctgagtgg attcccaccg     720
accttcaagg agacgagtca actgaagaca agctgccaa gaaaagcttt ccctctaaaa     780
ataaagctgt tgcggctgta ctcggaggcc agtgtcgctc ttctgaaatt gaataatccc     840 aagggttttcc aagagctgaa caagcagacc aagaagaaca tgaccatcga tgggaaggaa     900
ctgaccatca gccctgcgta tctgctgtgg gacctgagtg ccatcagcca gtccaagcag     960
gatgaggacg cgtctgccag ccgctttgag gataatgaag agctgaggta ctcgctgcga    1020
tctatcgaga gacacgcgcc atgggtacgg aatattttca ttgtcaccaa cgggcagatt    1080
ccatcctggc tgaaccttga caaccctcga gtgaccatag tgacccacca ggacattttc    1140
caaaatctga gccacttgcc tactttcagt tcccctgcta ttgaaagtca cattcaccgc    1200
```

```
atcgaagggc tgtcccagaa gtttatttat ctaaatgacg atgtcatgtt cggtaaggac    1260
gtctggccgg acgattttta cagccactcc aaaggtcaaa aggtttattt gacatggcct    1320
gtgccaaact gtgcagaggg ctgcccgggc tcctggataa aggacggcta ttgtgataag    1380
gcctgtaata cctcaccctg tgactgggat ggcggaaact gctctggtaa tactgcaggg    1440
aaccggtttg ttgcaagagg tgggggtacc gggaatattg gagctggaca gcactggcag    1500
tttggtggag gaataaacac catctcttac tgtaaccaag gatgtgcaaa ctcctggctg    1560
gctgacaagt tctgtgacca agcctgtaac gtcttatcct gcgggtttga tgctggtgac    1620
tgtggacaag atcattttca tgaattgtat aaagtaaaca ttctcccaaa ccagactcac    1680
tatgttgtcc ccaaaggtga atacctgtct tatttcagct ttgcaaacat agccagaaaa    1740
agaattgaag ggacctacag cgacaacccc atcatccgcc acgcgtccat tgcaaacaag    1800
tggaaaaccc tacacctgat aatgcccggg gggatgaacg ccaccacgat ctattttaac    1860
ctcactcttc aaaacgccaa cgacgaagag ttcaagatcc agatagcagt agaggtggac    1920
acgagggagg cgcccaaact gaattctaca acccagaagg cctatgaaag tttggttagc    1980
ccagtgacac ctcttcctca ggctgacgtc ccttttgaag atgtcccaa agagaaacgc    2040 ttccccaaga tcaggagaca tgatgtaaat gcaacaggga gattccaaga ggaggtgaaa    2100
atcccccggg taaatatttc actccttccc aaagaggccc aggtgaggct gagcaacttg    2160
gatttgcaac tagaacgtgg agacatcact ctgaaaggat ataacttgtc caagtcagcc    2220
ctgctaaggt ctttcctggg gaattcacta gatactaaaa taaaacctca agctaggacc    2280
gatgaaacaa aaggcaacct ggaggtccca caggaaaacc cttctcacag acgtccacat    2340
ggctttgctg gtgaacacag atcagagaga tggactgccc cagcagagac agtgaccgtg    2400
aaaggccgtg accacgcttt gaatccaccc ccggtgttgg agaccaatgc aagattggcc    2460
cagcctacac taggcgtgac tgtgtccaaa gagaaccttt caccgctgat cgttccccca    2520
gaaagccact tgccaaaaga agaggagagt gacagggcag aaggcaatgc tgtacctgta    2580
aaggagttag tgcctggcag acggttgcag cagaattatc caggcttttt gccctgggag    2640
aaaaaaaagt atttccaaga ccttcttgat gaggaagagt cattgaagac ccagttggcg    2700
tactttacag accgcaaaca taccggggagg caactaaaag atacatttgc agactccctc    2760
cgatacgtca ataaaattct caacagcaag tttggattca catccaggaa agtccctgca    2820
cacatgccgc acatgattga caggatcgtt atgcaagaac tccaagatat gttccctgaa    2880
gaatttgaca agacttcatt tcacaaggtg cgtcactctg aggacatgca gtttgccttc    2940
tcctactttt attacctcat gagtgcagtt cagcccctca atatttccca agtctttcat    3000
gaagtagaca cagaccaatc tggtgtcttg tctgataggg aaatccgaac wctgccacg    3060 agaattcacg acctaccttt aagcttgcag gatttgacag gtttggaaca catgttaata    3120
aattgctcaa aaatgctccc cgctaatatc actcaactca caacatccc accgactcag    3180 gaagcatact acgaccccaa cctgcctccg tcactaagag tcttgtcac caactgtaag    3240 ccagtaactg acaagatcca caagcctat aaagacaaga caaatacag gtttgaaatc    3300 atgggagagg aagaaatcgc tttcaagatg atacgaacca atgtttctca tgtggttggt    3360
cagttggatg acatcagaaa aaaccccagg aagttcgttt gtctgaatga caacattgac    3420
cacaaccata aagatgcccg gacagtgaag gctgtcctca gggacttcta tgagtccatg    3480
tttcccatac cttcccagtt tgagctgcca agagagtatc ggaaccgctt tctgcacatg    3540
catgagctcc aagaatggcg ggcatatcga gacaagctga agttttggac ccactgcgta    3600
```

-continued

```
ctagcaacgt tgattatatt tactatattc tcatttttg ctgaacagat aattgctctg   3660
aagcgaaaga tatttcccag gaggaggata cacaaagaag ctagtccaga ccgaatcagg   3720
gtgtagaaga tcttcatttg aaagtcacct accttagcat ctgtgaacat ctccctcctc   3780
gacaccacag cggagtccct gtgatgtggc acagaggcag cctcgtgggg agaagggaca   3840
tcgtgcagac cggttcttc tgcaatggga agagagccca ctgacctgga attattcagc    3900
acactaagaa cctgtgtcaa tagcttgtac agcttgtact tttaaaggat tgccgaagg    3960 acctgtcggc ttgttgacaa accctccctg caagctgct ggtttcttcc cccagttact    4020
gcagactgag aaaccagtcc atcttgaaag caagtgcgga ggggcccag tctttgcatt    4080 ccaaagcttt ccagcataat ttctggcttg tctcctcctt tgatccattt cccatttttt   4140
tttaaaaaac aataagtggc tactaagtta gtcattctca cttctcaaaa taacaaatca   4200
ggatgtcaaa acatttgtat agatcttatt taaataatat agaacgatta cttctttagc   4260
ctatctaaat tattgatttt tattaacagt caagtggtct tgaaccgcta acaactactg   4320
aagagctcga gattgacgtt gaaagtgctt tgagcttgtt taactcattc cccaagaata   4380
ctgtgacctc gtgtgcgggc ctgattgcga agggctagtg tcacgtagca gtgctgctca   4440
ccggatgtaa ttatgtcgtg gaaatgtaca tacagacaaa agtgcctcac ttcagaaatg   4500
agtagtgctg atggcaccag cgagtgatgg tgtccatttg gaaacccatg ataccttcca   4560
atgcccaccc tgcttacttt atacagagca ggggttaacc aacttctgtc aaagaacagt   4620
aaagaacttg agatacatcc atctttgtca aatagttttc cttgctaaca tttattattg   4680
ttggtgtttt gggaggttta ttttatttta ttgctttgtt attttttcaag acggggattc   4740 tctgtgtagc tctggctgtt tggtaattca ctctaaagac caggctggcc ttgaacttag   4800
agattcacct gcttctgctt cctgaatggt aggacatgtg cccacattgc ctacccaccc   4860
cccttttggg gggggtgagc aactcaataa aaagatgaaa acctgcttta gtttgcagct   4920
atacaaaagc agcaggcctc agccagactt gaccccgggg gccattgttg gcccacggga   4980
gaatcatttt tgacgtgggt aagcaaaccc tgatattggt catgctgtgt tatgtcatta   5040
tgtggtggtt ttgaattttg gaagatattt tcagtcatga tttcagtagt attcctccaa   5100
aatggcacac attttgtaa taagaacttg aaatgtaaat attgtgtttg tgctgtaaat   5160
tttgtgtatt tcaaaactg aagtttcata aaaaaacaca cttattggaa aaaaaaaaaa   5220
aaaaaaaaa                                                          5229
```

<210> SEQ ID NO 9
<211> LENGTH: 908
<212> TYPE: PRT
<213> ORGANISM: Mus musculus

<400> SEQUENCE: 9

```
Met Leu Phe Lys Leu Leu Gln Arg Gln Thr Tyr Thr Cys Leu Ser His
1               5                   10                  15

Arg Tyr Gly Leu Tyr Val Cys Phe Val Gly Val Val Thr Ile Val
            20                  25                  30

Ser Ala Phe Gln Phe Gly Glu Val Val Leu Glu Trp Ser Arg Asp Gln
        35                  40                  45

Tyr His Val Leu Phe Asp Ser Tyr Arg Asp Asn Ile Ala Gly Lys Ser
    50                  55                  60

Phe Gln Asn Arg Leu Cys Leu Pro Met Pro Ile Asp Val Val Tyr Thr
65                  70                  75                  80
```

```
Trp Val Asn Gly Thr Asp Leu Glu Leu Leu Lys Glu Leu Gln Gln Val
                85                  90                  95
Arg Glu His Met Glu Glu Gln Arg Ala Met Arg Glu Thr Leu Gly
            100                 105                 110
Lys Asn Thr Thr Glu Pro Thr Lys Lys Ser Glu Lys Gln Leu Glu Cys
            115                 120                 125
Leu Leu Thr His Cys Ile Lys Val Pro Met Leu Val Leu Asp Pro Ala
    130                 135                 140
Leu Pro Ala Thr Ile Thr Leu Lys Asp Leu Pro Thr Leu Tyr Pro Ser
145                 150                 155                 160
Phe His Ala Ser Ser Asp Met Phe Asn Val Ala Lys Pro Lys Asn Pro
                165                 170                 175
Ser Thr Asn Val Pro Val Val Phe Asp Thr Lys Asp Val Glu
            180                 185                 190
Asp Ala His Ala Gly Pro Phe Lys Gly Gln Gln Thr Asp Val Trp
            195                 200                 205
Arg Ala Tyr Leu Thr Thr Asp Lys Asp Ala Pro Gly Leu Val Leu Ile
    210                 215                 220
Gln Gly Leu Ala Phe Leu Ser Gly Phe Pro Pro Thr Phe Lys Glu Thr
225                 230                 235                 240
Ser Gln Leu Lys Thr Lys Leu Pro Arg Lys Ala Phe Pro Leu Lys Ile
            245                 250                 255
Lys Leu Leu Arg Leu Tyr Ser Glu Ala Ser Val Ala Leu Leu Lys Leu
            260                 265                 270
Asn Asn Pro Lys Gly Phe Gln Glu Leu Asn Lys Gln Thr Lys Lys Asn
            275                 280                 285
Met Thr Ile Asp Gly Lys Glu Leu Thr Ile Ser Pro Ala Tyr Leu Leu
    290                 295                 300
Trp Asp Leu Ser Ala Ile Ser Gln Ser Lys Gln Asp Glu Asp Ala Ser
305                 310                 315                 320
Ala Ser Arg Phe Glu Asp Asn Glu Glu Leu Arg Tyr Ser Leu Arg Ser
                325                 330                 335
Ile Glu Arg His Ala Pro Trp Val Arg Asn Ile Phe Ile Val Thr Asn
                340                 345                 350
Gly Gln Ile Pro Ser Trp Leu Asn Leu Asp Asn Pro Arg Val Thr Ile
            355                 360                 365
Val Thr His Gln Asp Ile Phe Gln Asn Leu Ser His Leu Pro Thr Phe
    370                 375                 380
Ser Ser Pro Ala Ile Glu Ser His Ile His Arg Ile Glu Gly Leu Ser
385                 390                 395                 400
Gln Lys Phe Ile Tyr Leu Asn Asp Asp Val Met Phe Gly Lys Asp Val
                405                 410                 415
Trp Pro Asp Asp Phe Tyr Ser His Ser Lys Gly Gln Lys Val Tyr Leu
            420                 425                 430
Thr Trp Pro Val Pro Asn Cys Ala Glu Gly Cys Pro Gly Ser Trp Ile
            435                 440                 445
Lys Asp Gly Tyr Cys Asp Lys Ala Cys Asn Thr Ser Pro Cys Asp Trp
    450                 455                 460
Asp Gly Gly Asn Cys Ser Gly Asn Thr Ala Gly Asn Arg Phe Val Ala
465                 470                 475                 480
Arg Gly Gly Gly Thr Gly Asn Ile Gly Ala Gly Gln His Trp Gln Phe
                485                 490                 495
```

-continued

Gly Gly Gly Ile Asn Thr Ile Ser Tyr Cys Asn Gln Gly Cys Ala Asn
              500                 505                 510

Ser Trp Leu Ala Asp Lys Phe Cys Asp Gln Ala Cys Asn Val Leu Ser
        515                 520                 525

Cys Gly Phe Asp Ala Gly Asp Cys Gly Gln Asp His Phe His Glu Leu
        530                 535                 540

Tyr Lys Val Thr Leu Leu Pro Asn Gln Thr His Tyr Val Val Pro Lys
545                 550                 555                 560

Gly Glu Tyr Leu Ser Tyr Phe Ser Phe Ala Asn Ile Ala Arg Lys Arg
                565                 570                 575

Ile Glu Gly Thr Tyr Ser Asp Asn Pro Ile Ile Arg His Ala Ser Ile
            580                 585                 590

Ala Asn Lys Trp Lys Thr Leu His Leu Ile Met Pro Gly Gly Met Asn
        595                 600                 605

Ala Thr Thr Ile Tyr Phe Asn Leu Thr Leu Gln Asn Ala Asn Asp Glu
    610                 615                 620

Glu Phe Lys Ile Gln Ile Ala Val Glu Val Asp Thr Arg Glu Ala Pro
625                 630                 635                 640

Lys Leu Asn Ser Thr Thr Gln Lys Ala Tyr Glu Ser Leu Val Ser Pro
                645                 650                 655

Val Thr Pro Leu Pro Gln Ala Asp Val Pro Phe Glu Asp Val Pro Lys
            660                 665                 670

Glu Lys Arg Phe Pro Lys Ile Arg Arg His Asp Val Asn Ala Thr Gly
        675                 680                 685

Arg Phe Gln Glu Glu Val Lys Ile Pro Arg Val Asn Ile Ser Leu Leu
    690                 695                 700

Pro Lys Glu Ala Gln Val Arg Leu Ser Asn Leu Asp Leu Gln Leu Glu
705                 710                 715                 720

Arg Gly Asp Ile Thr Leu Lys Gly Tyr Asn Leu Ser Lys Ser Ala Leu
                725                 730                 735

Leu Arg Ser Phe Leu Gly Asn Ser Leu Asp Thr Lys Ile Lys Pro Gln
            740                 745                 750

Ala Arg Thr Asp Glu Thr Lys Gly Asn Leu Glu Val Pro Gln Glu Asn
        755                 760                 765

Pro Ser His Arg Arg Pro His Gly Phe Ala Gly Glu His Arg Ser Glu
    770                 775                 780

Arg Trp Thr Ala Pro Ala Glu Thr Val Thr Val Lys Gly Arg Asp His
785                 790                 795                 800

Ala Leu Asn Pro Pro Val Leu Glu Thr Asn Ala Arg Leu Ala Gln
                805                 810                 815

Pro Thr Leu Gly Val Thr Val Ser Lys Glu Asn Leu Ser Pro Leu Ile
            820                 825                 830

Val Pro Pro Glu Ser His Leu Pro Lys Glu Glu Ser Asp Arg Ala
        835                 840                 845

Glu Gly Asn Ala Val Pro Val Lys Glu Leu Val Pro Gly Arg Arg Leu
    850                 855                 860

Gln Gln Asn Tyr Pro Gly Phe Leu Pro Trp Glu Lys Lys Lys Tyr Phe
865                 870                 875                 880

Gln Asp Leu Leu Asp Glu Glu Ser Leu Lys Thr Gln Leu Ala Tyr
                885                 890                 895

Phe Thr Asp Arg Lys His Thr Gly Arg Gln Leu Lys
            900                 905

<210> SEQ ID NO 10
<211> LENGTH: 328
<212> TYPE: PRT
<213> ORGANISM: Mus musculus

<400> SEQUENCE: 10

Asp Thr Phe Ala Asp Ser Leu Arg Tyr Val Asn Lys Ile Leu Asn Ser
1               5                   10                  15

Lys Phe Gly Phe Thr Ser Arg Lys Val Pro Ala His Met Pro His Met
            20                  25                  30

Ile Asp Arg Ile Val Met Gln Glu Leu Gln Asp Met Phe Pro Glu Glu
        35                  40                  45

Phe Asp Lys Thr Ser Phe His Lys Val Arg His Ser Glu Asp Met Gln
    50                  55                  60

Phe Ala Phe Ser Tyr Phe Tyr Tyr Leu Met Ser Ala Val Gln Pro Leu
65                  70                  75                  80

Asn Ile Ser Gln Val Phe His Glu Val Asp Thr Asp Gln Ser Gly Val
                85                  90                  95

Leu Ser Asp Arg Glu Ile Arg Thr Leu Ala Thr Arg Ile His Asp Leu
            100                 105                 110

Pro Leu Ser Leu Gln Asp Leu Thr Gly Leu Glu His Met Leu Ile Asn
        115                 120                 125

Cys Ser Lys Met Leu Pro Ala Asn Ile Thr Gln Leu Asn Asn Ile Pro
130                 135                 140

Pro Thr Gln Glu Ala Tyr Tyr Asp Pro Asn Leu Pro Pro Val Thr Lys
145                 150                 155                 160

Ser Leu Val Thr Asn Cys Lys Pro Val Thr Asp Lys Ile His Lys Ala
                165                 170                 175

Tyr Lys Asp Lys Asn Lys Tyr Arg Phe Glu Ile Met Gly Glu Glu
            180                 185                 190

Ile Ala Phe Lys Met Ile Arg Thr Asn Val Ser His Val Val Gly Gln
        195                 200                 205

Leu Asp Asp Ile Arg Lys Asn Pro Arg Lys Phe Val Cys Leu Asn Asp
    210                 215                 220

Asn Ile Asp His Asn His Lys Asp Ala Arg Thr Val Lys Ala Val Leu
225                 230                 235                 240

Arg Asp Phe Tyr Glu Ser Met Phe Pro Ile Pro Ser Gln Phe Glu Leu
                245                 250                 255

Pro Arg Glu Tyr Arg Asn Arg Phe Leu His Met His Glu Leu Gln Glu
            260                 265                 270

Trp Arg Ala Tyr Arg Asp Lys Leu Lys Phe Trp Thr His Cys Val Leu
        275                 280                 285

Ala Thr Leu Ile Ile Phe Thr Ile Phe Ser Phe Phe Ala Glu Gln Ile
    290                 295                 300

Ile Ala Leu Lys Arg Lys Ile Phe Pro Arg Arg Ile His Lys Glu
305                 310                 315                 320

Ala Ser Pro Asp Arg Ile Arg Val
                325

<210> SEQ ID NO 11
<211> LENGTH: 2070
<212> TYPE: DNA
<213> ORGANISM: Mus musculus
<220> FEATURE:
<221> NAME/KEY: misc_feature
<222> LOCATION: (186)..(186)
<223> OTHER INFORMATION: n is a, t, c, or g

<400> SEQUENCE: 11

```
gtgagaccct aggagcaatg gccggcggc tggctggctt cctgatgttg ctgggctcg      60
cgtcgcaggg gcccgcgccg gcatgtgccg gaagatgaa ggtggtggag gagcctaaca     120
cattcggtg agcggatcac ggtcctgcgg cttggggacc gagcctggct ggttcttctg    180
accttntcaa ttccataggc tgaataaccc gttcttgccc caggcaagcc gccttcagcc    240
caagagagag ccttcagctg tatcccgcaa attaagagaa attaatttca aacgatttag    300
aaagtattct agccaggcga tgatggcgca cgcctttaat cccagcactt gggaggcaga    360
ggcaggcaga tttccgagtt caaggccatc agaactgact gtacatctta gtacagttta    420
gcatgtgatc agagatctga atcacaaagc tgggcctgcg tggtaaagca ggtcctttct    480
aataaggttg cagtttagat tttctttctt aactctttta ttctttgaga cagggtttct    540
caacagtggg tgtcctggaa ctcacttttg taaaccaggc tgcccttaaa ctcacaaagc    600
tctgtcagcc tctgcctcct gagtgctggg attaaaggtc cacaccctgt tcattcattt    660
ttaatttttg agactgggtc tcattatgtg gccctagaca gatactgaga gcctcctcca    720
caggaacaag catgggaatc ctgccacaga caaccagttc tgtggtctgg agatgagttt    780
gtcagtccct aggagttagg tcagcctgcc tctgcattcc caataattta ggaaaggagc    840
ttggggcgtt ctggccttga tggttagtgc cctcctgcca accttagctt ccagctttag    900
gggtagcaga gtttataccg atgctaaact gctgttgtgt tcttcccag ggcccctgca    960
tctcttcaga cttgctggca agtgctttag cctagtggag tccacgtgag tgccaggctg   1020
gtgggtggag tgggcggagt ctgcagagct cctgatgtgc ctgtgtttcc caggtacaag   1080
tatgaattct gccctttcca caacgtcacc cagcacgagc agaccttccg ctggaatgcc   1140
tacagcggga tccttggcat ctggcatgag tgggaaatca tcaacaatac cttcaagggc   1200
atgtggatga ctgatgggga ctcctgccac tcccggagcc ggcagagcaa ggtggagctc   1260
acctgtggaa agatcaaccg actggcccac gtgtctgagc caagcacctg tgtctatgca   1320
ttgacattcg agacccctct tgtttgccat ccccactctt tgttagtgta tccaactctg   1380
tcagaagccc tgcagcagcc cttggaccag gtggaacagg acctggcaga tgaactgatc   1440
acaccacagg gctatgagaa gttgctaagg gtacttttg aggatgctgg ctacttaaag   1500
gtcccaggag aaacccatcc cacccagctg gcaggaggtt ccaagggcct ggggcttgag   1560
actctggaca actgtagaaa ggcacatgca gagctgtcac aggaggtaca agactgacg    1620
agtctgctgc aacagcatgg aatcccccac actcagccca caggtcagtc tgcctgccct   1680
ggtcagctgc cagccactcc ggggcctgca gcactgggc agatctttat tgctacccat    1740
tctggcagaa accactcact ctcagcacct gggtcagcag ctccccatag gtgcaatcgc   1800
agcagagcat ctgcggagtg acccaggact acgtgggaac atcctgtgag caaggtggcc   1860
acgaagaata gaaatatcct gagctttgag tgtcctttca cagagtgaac aaaactggtg   1920
tggtgtagac acggcttctt ttggcatatt ctagatcaga cagtgtcact gacaaacaag   1980
agggacctgc tggccagcct ttgttgtgcc caaagatcca gacaaaataa agattcaaag   2040
ttttaattaa aaaaaaaaaa aaaggaattc                                    2070
```

<210> SEQ ID NO 12
<211> LENGTH: 307
<212> TYPE: PRT
<213> ORGANISM: Mus musculus

<400> SEQUENCE: 12

```
Met Ala Gly Arg Leu Ala Gly Phe Leu Met Leu Leu Gly Leu Ala Ser
1               5                   10                  15

Gln Gly Pro Ala Pro Ala Cys Ala Gly Lys Met Lys Val Val Glu Glu
            20                  25                  30

Pro Asn Thr Phe Gly Leu Asn Asn Pro Phe Leu Pro Gln Ala Ser Arg
            35                  40                  45

Leu Gln Pro Lys Arg Glu Pro Ser Ala Val Ser Gly Pro Leu His Leu
        50                  55                  60

Phe Arg Leu Ala Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
            100                 105                 110

Ile Ile Asn Asn Thr Phe Lys Gly Met Trp Met Thr Asp Gly Asp Ser
            115                 120                 125

Cys His Ser Arg Ser Arg Gln Ser Lys Val Glu Leu Thr Cys Gly Lys
    130                 135                 140

Ile Asn Arg Leu Ala His Val Ser Glu Pro Ser Thr Cys Val Tyr Ala
145                 150                 155                 160

Leu Thr Phe Glu Thr Pro Leu Val Cys His Pro His Ser Leu Leu Val
                165                 170                 175

Tyr Pro Thr Leu Ser Glu Ala Leu Gln Gln Arg Leu Asp Gln Val Glu
            180                 185                 190

Gln Asp Leu Ala Asp Glu Leu Ile Thr Pro Gln Gly Tyr Glu Lys Leu
        195                 200                 205

Leu Arg Val Leu Phe Glu Asp Ala Gly Tyr Leu Lys Val Pro Gly Glu
210                 215                 220

Thr His Pro Thr Gln Leu Ala Gly Gly Ser Lys Gly Leu Gly Leu Glu
225                 230                 235                 240

Thr Leu Asp Asn Cys Arg Lys Ala His Ala Glu Leu Ser Gln Glu Val
                245                 250                 255

Gln Arg Leu Thr Ser Leu Leu Gln Gln His Gly Ile Pro His Thr Gln
            260                 265                 270

Pro Thr Glu Thr Thr His Ser Gln His Leu Gly Gln Gln Leu Pro Ile
        275                 280                 285

Gly Ala Ile Ala Ala Glu His Leu Arg Ser Asp Pro Gly Leu Arg Gly
    290                 295                 300

Asn Ile Leu
305
```

<210> SEQ ID NO 13
<211> LENGTH: 460
<212> TYPE: DNA
<213> ORGANISM: Rattus rattus

<400> SEQUENCE: 13

```
attcccacca acattcaagg agacgagtca gctgaagaca aaactgccag aaaatctttc      60
ttctaaaata aaactgttgc agctgtactc ggaggccagc gtcgctcttc tgaaattgaa     120
taaccccaaa ggtttccccg agctgaacaa gcagaccaag aagaacatga gcatcagtgg     180
gaaggaactg gccatcagcc ctgcctatct gctgtgggac ctgagcgcca tcagccagtc     240
caagcaggat gaagatgtgt ctgccagccg cttcgaggat aacgaagagc tgaggtactc     300
```

| | | |
|---|---|---|
| actgagatct atcgagagac atgattccat gagtccttta tgaattctgg ccatatcttc | 360 |
| aatcatgatc tcagtagtat tcctctgaaa tggcacacat ttttctaatg agaacttgaa | 420 |
| atgtaaatat tgtgtttgtg ctgtaaattt tgtgtatttc | 460 |

```
<210> SEQ ID NO 14
<211> LENGTH: 113
<212> TYPE: PRT
<213> ORGANISM: Rattus rattus

<400> SEQUENCE: 14

Phe Pro Pro Thr Phe Lys Glu Thr Ser Gln Leu Lys Thr Lys Leu Pro
1               5                   10                  15

Glu Asn Leu Ser Ser Lys Ile Lys Leu Leu Gln Leu Tyr Ser Glu Ala
            20                  25                  30

Ser Val Ala Leu Leu Lys Leu Asn Asn Pro Lys Gly Phe Pro Glu Leu
        35                  40                  45

Asn Lys Gln Thr Lys Lys Asn Met Ser Ile Ser Gly Lys Glu Leu Ala
    50                  55                  60

Ile Ser Pro Ala Tyr Leu Leu Trp Asp Leu Ser Ala Ile Ser Gln Ser
65                  70                  75                  80

Lys Gln Asp Glu Asp Val Ser Ala Ser Arg Phe Glu Asp Asn Glu Glu
                85                  90                  95

Leu Arg Tyr Ser Leu Arg Ser Ile Glu Arg His Asp Ser Met Ser Pro
            100                 105                 110

Leu

<210> SEQ ID NO 15
<211> LENGTH: 1105
<212> TYPE: DNA
<213> ORGANISM: Drosophila melanogaster
<220> FEATURE:
<221> NAME/KEY: misc_feature
<222> LOCATION: (903)..(903)
<223> OTHER INFORMATION: n is a, g, t, or c
<221> NAME/KEY: misc_feature
<222> LOCATION: (935)..(935)
<223> OTHER INFORMATION: n is a, g, t, or c
<221> NAME/KEY: misc_feature
<222> LOCATION: (1023)..(1023)
<223> OTHER INFORMATION: n is a, g, t, or c
<221> NAME/KEY: misc_feature
<222> LOCATION: (1035)..(1035)
<223> OTHER INFORMATION: n is a, g, t, or c
<221> NAME/KEY: misc_feature
<222> LOCATION: (1071)..(1071)
<223> OTHER INFORMATION: n is a, g, t, or c
<221> NAME/KEY: misc_feature
<222> LOCATION: (1100)..(1100)
<223> OTHER INFORMATION: n is a, g, t, or c

<400> SEQUENCE: 15
```

| | | |
|---|---|---|
| ctgcaggaat tcggcacgag gcggttcgat gacaagaatg agctgcggta ctctctgagg | 60 |
| tccctggaaa acacgccgc atggatcagg catgtgtaca tagtaaccaa tggccagatt | 120 |
| ccaagttggc tggatctcag ctacgaaagg gtcacggtgg tgccccacga agtcctggct | 180 |
| cccgatcccg accagctgcc caccttctcc agctcggcca tcgagacatt tctgcaccgc | 240 |
| ataccaaagc tgtccaagag gttcctctac ctcaacgacg acatattcct gggagctccg | 300 |
| ctgtatccgg aggacttgta cactgaagcg gagggagttc gcgtgtacca ggcatggatg | 360 |
| gtgcccggct gcgccttgga ttgccctgg acgtacatag tgatggagc ttgcgatcgg | 420 |

-continued

```
cactgcaaca ttgatgcgtg ccaatttgat ggaggcgact gcagtgaaac tgggccagcg    480
agcgatgccc acgtcattcc accaagcaaa gaagtgctcg aggtgcagcc tgccgctgtt    540
ccacaatcaa gagtccaccg atttcctcag atgggtctcc aaaagctgtt caggcgcagc    600
tctgccaatt ttaaggatgt tatgcggcac cgcaatgtgt ccacactcaa ggaactacgt    660
cgcattgtgg agcgttttaa caaggccaaa ctcatgtcgc tgaaccccga actggagacc    720
tccagctccg agccacagac aactcagcgc acgggctgc gcaaggagga ttttaagtct     780
tccaccgata tttactctca ctcgctgatt gccaccaata tgttgctgaa tagagcctat    840
ggctttaagg cacgccatgt cctggcgcac gtgggcttcc taattgacaa ggatattgtg    900
gangccatgc aacgacgttt taccagcgaa ttctngacac tggccattaa cgctttccga    960
gccccaacag atttgcagta cgcattcgct tactacttct ttctaatgag cgaaatccaa   1020
gtnatgagtg tagangaaat cttcgatgaa gtcgacaccg acggtttgg ncacctggtc    1080 ggatccagaa gtgcgaaccn tttta                                         1105
```

<210> SEQ ID NO 16
<211> LENGTH: 502
<212> TYPE: PRT
<213> ORGANISM: Drosophila melanogaster

<400> SEQUENCE: 16

```
Gly Thr Arg Arg Phe Asp Asp Lys Asn Glu Leu Arg Tyr Ser Leu Arg
1               5                   10                  15

Ser Leu Glu Lys His Ala Ala Trp Ile Arg His Val Tyr Ile Val Thr
            20                  25                  30

Asn Gly Gln Ile Pro Ser Trp Leu Asp Leu Ser Tyr Glu Arg Val Thr
        35                  40                  45

Val Val Pro His Glu Val Leu Ala Pro Asp Pro Asp Gln Leu Pro Thr
    50                  55                  60

Phe Ser Ser Ser Ala Ile Glu Thr Phe Leu His Arg Ile Pro Lys Leu
65                  70                  75                  80

Ser Lys Arg Phe Leu Tyr Leu Asn Asp Asp Ile Phe Leu Gly Ala Pro
                85                  90                  95

Leu Tyr Pro Glu Asp Leu Tyr Thr Glu Ala Glu Gly Val Arg Val Tyr
            100                 105                 110

Gln Ala Trp Met Val Pro Gly Cys Ala Leu Asp Cys Pro Trp Thr Tyr
        115                 120                 125

Ile Gly Asp Gly Ala Cys Asp Arg His Cys Asn Ile Asp Ala Cys Gln
    130                 135                 140

Phe Asp Gly Gly Asp Cys Ser Glu Thr Gly Pro Ala Ser Asp Ala His
145                 150                 155                 160

Val Ile Pro Pro Ser Lys Glu Val Leu Glu Val Gln Pro Ala Ala Val
                165                 170                 175

Pro Gln Ser Arg Val His Arg Phe Pro Gln Met Gly Leu Gln Lys Leu
            180                 185                 190

Phe Arg Arg Ser Ser Ala Asn Phe Lys Asp Val Met Arg His Arg Asn
        195                 200                 205

Val Ser Thr Leu Lys Glu Leu Arg Arg Ile Val Glu Arg Phe Asn Lys
    210                 215                 220

Ala Lys Leu Met Ser Leu Asn Pro Glu Leu Glu Thr Ser Ser Ser Glu
225                 230                 235                 240

Pro Gln Thr Thr Gln Arg His Gly Leu Arg Lys Glu Asp Phe Lys Ser
                245                 250                 255
```

```
Ser Thr Asp Ile Tyr Ser His Ser Leu Ile Ala Thr Asn Met Leu Leu
            260                 265                 270

Asn Arg Ala Tyr Gly Phe Lys Ala Arg His Val Leu Ala His Val Gly
            275                 280                 285

Phe Leu Ile Asp Lys Asp Ile Val Glu Ala Met Gln Arg Arg Phe His
            290                 295                 300

Gln Gln Ile Leu Asp Thr Ala His Gln Arg Phe Arg Ala Pro Thr Asp
305                 310                 315                 320

Leu Gln Tyr Ala Phe Ala Tyr Tyr Ser Phe Leu Met Ser Glu Thr Lys
                325                 330                 335

Val Met Ser Val Glu Glu Ile Phe Asp Glu Phe Asp Thr Asp Gly Ser
            340                 345                 350

Ala Thr Trp Ser Asp Arg Glu Val Arg Thr Phe Leu Thr Arg Ile Tyr
            355                 360                 365

Gln Pro Pro Leu Asp Trp Ser Ala Met Arg Tyr Phe Glu Glu Val Val
            370                 375                 380

Gln Asn Cys Thr Arg Asn Leu Gly Met His Leu Lys Val Asp Thr Val
385                 390                 395                 400

Glu His Ser Thr Leu Val Tyr Glu Arg Tyr Glu Asp Ser Asn Leu Pro
                405                 410                 415

Thr Ile Thr Arg Asp Leu Val Val Arg Cys Pro Leu Leu Ala Glu Ala
            420                 425                 430

Leu Ala Ala Asn Phe Ala Val Arg Pro Lys Tyr Asn Phe His Val Ser
            435                 440                 445

Pro Lys Arg Thr Ser His Ser Asn Phe Met Met Leu Thr Ser Asn Leu
            450                 455                 460

Thr Glu Val Val Glu Ser Leu Asp Arg Leu Arg Arg Asn Pro Arg Lys
465                 470                 475                 480

Phe Asn Cys Ile Asn Asp Asn Leu Asp Ala Asn Arg Gly Glu Asp Asn
                485                 490                 495

Glu Asp Gly Ala Pro Ser
            500

<210> SEQ ID NO 17
<211> LENGTH: 2183
<212> TYPE: DNA
<213> ORGANISM: Homo sapiens

<400> SEQUENCE: 17
atggcgacct ccacgggtcg ctggcttctc ctccggcttg cactattcgg cttcctctgg      60
gaagcgtccg gcggcctcga ctcgggggcc tcccgcgacg acgacttgct actgccctat     120
ccacgcgcgc gcgcgcgcct cccccgggac tgcacacggg tgcgcgccgg caaccgcgag     180
cacgagagtt ggcctccgcc tcccgcgact cccggcgccg gcgtctggcc gtgcgcacc      240 ttcgtgtcgc acttcaggga ccgcgcggtg gccggccacc tgacgcgggc cgttgagccc     300
ctgcgcacct tctcggtgct ggagcccggt ggacccggcg ctgcgcggc gagacgacgc      360 gccaccgtgg aggagacggc gcgggcggcc gactgccgtg tcgcccagaa cggcggcttc     420
ttccgcatga actcgggcga gtgcctgggg aacgtggtga cgacgagcg gcgggtgagc      480 agctccgggg ggctgcagaa cgcgcagttc gggatccgcc gcgacgggac cctggtcacc     540
gggtacctgt ctgaggagga ggtgctggac actgagaacc catttgtgca gctgctgagt     600
ggggtcgtgt ggctgattcg taatggaagc atctacatca cgagagccaa agccacagag     660
```

-continued

```
tgtgacgaga cacaggagac aggttccttt agcaaatttg tgaatgtgat atcagccagg    720
acggccattg gccacgaccg gaaagggcag ctggtgctct tcatgcaga cggccatacg    780 gagcagcgtg gcatcaacct gtgggaaatg gcggagttcc tgctgaaaca ggacgtggtc    840
aacgccatca acctggatgg gggtggctct gccacctttg tgctcaacgg gaccttggcc    900
agttacccgt cagatcactg ccaggacaac atgtggcgct gtccccgcca agtgtccacc    960
gtggtgtgtg tgcacgaacc ccgctgccag ccgcctgact gccacggcca cgggacctgc   1020
gtggacgggc actgccaatg caccgggcac ttctggcggg tcccggctg tgatgagctg   1080 gactgtggcc cctctaactg cagccagcac ggactgtgca cggagaccgg ctgccgctgt   1140
gatgccggat ggaccgggtc caactgcagt gaagagtgtc cccttggctg catgggccg   1200 ggctgccaga ggcgttgtaa gtgtgagcac cattgtccct gtgaccccaa gactggcaac   1260
tgcagcgtct ccagagtaaa gcagtgtctc cagccacctg aagccaccct gagggcggga   1320
gaactctcct ttttcaccag gaccgcctgg ctagccctca ccctggcgct ggccttcctc   1380
ctgctgatca gcattgcagc aaacctgtcc ttgctcctgt ccagagcaga gaggaaccgg   1440
cgcctgcatg gggactatgc ataccacccg ctgcaggaga tgaacgggga gcctctggcc   1500
gcagagaagg agcagccagg gggcgcccac aacccctttca aggactgaag cctcaagctg   1560 cccgggggtgg cacgtcgcga aagcttgttt ccccacggtc tggcttctgc aggggaaatt   1620
tcaaggccac tggcgtggac catctgggtg tcctcaatgg cccctgtggg gcagccaagt   1680
tcctgatagc acttgtgcct cagcccctca cctggccacc tgccagggca cctgcaaccc   1740
tagcaatacc atgctcgctg gagaggctca gctgcctgct tctcgcctgc ctgtgtctgc   1800
tgccgagaag cccgtgcccc cgggagggct gccgcactgc caaagagtct ccctcctcct   1860
ggggaagggg ctgccaacga accagactca gtgaccacgt catgacagaa cagcacatcc   1920
tggccagcac ccctggctgg agtgggttaa agggacgagt ctgccttcct ggctgtgaca   1980
cgggacccct tttctacaga cctcatcact ggatttgcca actagaattc gatttcctgt   2040
cataggaagc tccttggaag aagggatggg gggatgaaat catgtttaca gacctgtttt   2100
gtcatcctgc tgccaagaag ttttttaatc acttgaataa attgatataa taaaaggagc   2160
caccaggtgg tgtgtggatt ctg                                         2183
```

<210> SEQ ID NO 18
<211> LENGTH: 515
<212> TYPE: PRT
<213> ORGANISM: Homo sapiens

<400> SEQUENCE: 18

```
Met Ala Thr Ser Thr Gly Arg Trp Leu Leu Arg Leu Ala Leu Phe
1               5                  10                  15

Gly Phe Leu Trp Glu Ala Ser Gly Gly Leu Asp Ser Gly Ala Ser Arg
            20                  25                  30

Asp Asp Asp Leu Leu Leu Pro Tyr Pro Arg Ala Arg Ala Arg Leu Pro
        35                  40                  45

Arg Asp Cys Thr Arg Val Arg Ala Gly Asn Arg Glu His Glu Ser Trp
    50                  55                  60

Pro Pro Pro Ala Thr Pro Gly Ala Gly Gly Leu Ala Val Arg Thr
65                  70                  75                  80

Phe Val Ser His Phe Arg Asp Arg Ala Val Ala Gly His Leu Thr Arg
                85                  90                  95

Ala Val Glu Pro Leu Arg Thr Phe Ser Val Leu Glu Pro Gly Gly Pro
```

-continued

```
                  100                 105                 110
Gly Gly Cys Ala Ala Arg Arg Ala Thr Val Glu Thr Ala Arg
            115                 120                 125
Ala Ala Asp Cys Arg Val Ala Gln Asn Gly Gly Phe Phe Arg Met Asn
130                 135                 140
Ser Gly Glu Cys Leu Gly Asn Val Val Ser Asp Glu Arg Arg Val Ser
145                 150                 155                 160
Ser Ser Gly Gly Leu Gln Asn Ala Gln Phe Gly Ile Arg Arg Asp Gly
                165                 170                 175
Thr Leu Val Thr Gly Tyr Leu Ser Glu Glu Val Leu Asp Thr Glu
            180                 185                 190
Asn Pro Phe Val Gln Leu Leu Ser Gly Val Val Trp Leu Ile Arg Asn
            195                 200                 205
Gly Ser Ile Tyr Ile Asn Glu Ser Gln Ala Thr Glu Cys Asp Glu Thr
            210                 215                 220
Gln Glu Thr Gly Ser Phe Ser Lys Phe Val Asn Val Ile Ser Ala Arg
225                 230                 235                 240
Thr Ala Ile Gly His Asp Arg Lys Gly Gln Leu Val Leu Phe His Ala
                245                 250                 255
Asp Gly His Thr Glu Gln Arg Gly Ile Asn Leu Trp Glu Met Ala Glu
                260                 265                 270
Phe Leu Leu Lys Gln Asp Val Val Asn Ala Ile Asn Leu Asp Gly Gly
            275                 280                 285
Gly Ser Ala Thr Phe Val Leu Asn Gly Thr Leu Ala Ser Tyr Pro Ser
            290                 295                 300
Asp His Cys Gln Asp Asn Met Trp Arg Cys Pro Arg Gln Val Ser Thr
305                 310                 315                 320
Val Val Cys Val His Glu Pro Arg Cys Gln Pro Pro Asp Cys His Gly
                325                 330                 335
His Gly Thr Cys Val Asp Gly His Cys Gln Cys Thr Gly His Phe Trp
                340                 345                 350
Arg Gly Pro Gly Cys Asp Glu Leu Asp Cys Gly Pro Ser Asn Cys Ser
            355                 360                 365
Gln His Gly Leu Cys Thr Glu Thr Gly Cys Arg Cys Asp Ala Gly Trp
            370                 375                 380
Thr Gly Ser Asn Cys Ser Glu Glu Cys Pro Leu Gly Trp His Gly Pro
385                 390                 395                 400
Gly Cys Gln Arg Arg Cys Lys Cys Glu His His Cys Pro Cys Asp Pro
                405                 410                 415
Lys Thr Gly Asn Cys Ser Val Ser Arg Val Lys Gln Cys Leu Gln Pro
                420                 425                 430
Pro Glu Ala Thr Leu Arg Ala Gly Glu Leu Ser Phe Phe Thr Arg Thr
            435                 440                 445
Ala Trp Leu Ala Leu Thr Leu Ala Leu Ala Phe Leu Leu Ile Ser
            450                 455                 460
Ile Ala Ala Asn Leu Ser Leu Leu Leu Ser Arg Ala Glu Arg Asn Arg
465                 470                 475                 480
Arg Leu His Gly Asp Tyr Ala Tyr His Pro Leu Gln Glu Met Asn Gly
                485                 490                 495
Glu Pro Leu Ala Ala Glu Lys Glu Gln Pro Gly Gly Ala His Asn Pro
            500                 505                 510
Phe Lys Asp
515
```

<210> SEQ ID NO 19
<211> LENGTH: 2005
<212> TYPE: DNA
<213> ORGANISM: Mus musculus

<400> SEQUENCE: 19

```
gtttcccgcg acgatgacct gctgctgcct tacccactag cgcgcagacg tccctcgcga      60
gactgcgccc gggtgcgctc aggtagccca gagcaggaga gctggcctcc gccacctctg     120
gccacccacg aacccgggc gccaagccac cacgcgccg tgcgcacctt cgtgtcgcac       180
ttcgagggc gcgcggtggc cggccacctg acgcgggtcg ccgatcccct acgcactttc      240
tcggtgctgg agcccggagg agccggggc tgcggcggca gaagcgccgc ggctactgtg      300
gaggacacag ccgtccgggc cggttgccgc atcgctcaga acggtggctt cttccgcatg     360
agcactggcg agtgcttggg gaacgtggtg agcgacgggc ggctggtgag cagctcaggg     420
ggactgcaga acgcgcagtt cggtatccga cgcgatggaa ccatagtcac cgggtcctgt     480
cttgaagaag aggttctgga tcccgtgaat ccgttcgtgc agctgctgag cggagtcgtg     540
tggctcatcc gcaatggaaa catctacatc aacgagagcc aagccatcga gtgtgacgag     600
acacaggaga caggttcttt tagcaaattt gtgaatgtga tgtcagccag acagccgtg     660
ggtcatgacc gtgaggggca gcttatcctc ttccatgctg atggacagac ggaacagcgt     720
ggccttaacc tatgggagat ggcagagttc ctgcgtcaac aagatgtcgt caatgccatc     780
aacctggatg gaggcggttc tgctactttt gtgctcaatg gaccctggc cagttaccct     840
tcagatcact gccaggacaa catgtggcgc tgtccccgcc aagtgtccac tgtggtgtgt     900
gtgcatgaac cgcgctgcca gccacccgac tgcagtggcc atgggacctg tgtggatggc     960
cactgtgaat gcaccagcca cttctggcgg ggcgaggcct gcagcgagct ggactgtggc    1020
ccctccaact gcagccagca tgggctgtgc acagctggct gccactgtga tgctgggtgg    1080
acaggatcca actgcagtga agagtgtcct ctgggctggt atgggccagg ttgccagagg    1140
ccctgccagt gtgagcacca gtgtttctgt gaccgcaga ctggcaactg cagcatctcc     1200
caagtgaggc agtgtctcca gccaactgag gctacgccga gggcaggaga gctggcctct    1260
ttcaccagga ccacctggct agccctcacc ctgacactaa ttttcctgct gctgatcagc    1320
actggggtca acgtgtcctt gttcctgggc tccagggccg agaggaaccg gcacctcgac    1380
ggggactatg tgtatcaccc actgcaggag gtgaacgggg aagcgctgac tgcagagaag    1440
gagcacatgg aggaaactag caacccttc aaggactgaa gagctgcccc aacggcatgc    1500
tccagataat cttgtccctg ctcctcactt ccacagggga cattgtgagg ccactggcat    1560
ggatgctatg cacccaccc tttgctggcc atattcctcc tgtccccatg ctgtggctca    1620
tgccaaccta gcaataagga gctctggaga gcctgcacct gcctcccgct cgcctatatc    1680
tgctgcccag aggcctgtct cgcacagggg tctcgccact gccaaagact cccaggaagt    1740
caaagactcc cagtaatcca ctagcaaatg gaactctgta acgccatcat aacaagagtg    1800
gccactctcc gcgtgcacag gtatgaaata taaatcctta cacacacaca cacacacacc    1860
ctcggctcag ccacggcact cgccttttat acagcgtcat cgctggacag ccaactagaa    1920
ctctgcatcc tgtcacagga agcacctcat aagaaggaat ggggagggaa ggcagtcgcc    1980
ttgttttcag accttagccg aattc                                           2005
```

<210> SEQ ID NO 20

-continued

<211> LENGTH: 492
<212> TYPE: PRT
<213> ORGANISM: Mus musculus

<400> SEQUENCE: 20

```
Val Ser Arg Asp Asp Asp Leu Leu Pro Tyr Pro Leu Ala Arg Arg
1               5                   10                  15

Arg Pro Ser Arg Asp Cys Ala Arg Val Arg Ser Gly Ser Pro Glu Gln
            20                  25                  30

Glu Ser Trp Pro Pro Pro Leu Ala Thr His Glu Pro Arg Ala Pro
        35                  40                  45

Ser His His Ala Ala Val Arg Thr Phe Val Ser His Phe Glu Gly Arg
    50                  55                  60

Ala Val Ala Gly His Leu Thr Arg Val Ala Asp Pro Leu Arg Thr Phe
65                  70                  75                  80

Ser Val Leu Glu Pro Gly Gly Ala Gly Gly Cys Gly Gly Arg Ser Ala
                85                  90                  95

Ala Ala Thr Val Glu Asp Thr Ala Val Arg Ala Gly Cys Arg Ile Ala
            100                 105                 110

Gln Asn Gly Gly Phe Phe Arg Met Ser Thr Gly Glu Cys Leu Gly Asn
        115                 120                 125

Val Val Ser Asp Gly Arg Leu Val Ser Ser Gly Gly Leu Gln Asn
130                 135                 140

Ala Gln Phe Gly Ile Arg Arg Asp Gly Thr Ile Val Thr Gly Ser Cys
145                 150                 155                 160

Leu Glu Glu Glu Val Leu Asp Pro Val Asn Pro Phe Val Gln Leu Leu
                165                 170                 175

Ser Gly Val Val Trp Leu Ile Arg Asn Gly Asn Ile Tyr Ile Asn Glu
            180                 185                 190

Ser Gln Ala Ile Glu Cys Asp Glu Thr Gln Glu Thr Gly Ser Phe Ser
        195                 200                 205

Lys Phe Val Asn Val Met Ser Ala Arg Thr Ala Val Gly His Asp Arg
210                 215                 220

Glu Gly Gln Leu Ile Leu Phe His Ala Asp Gly Gln Thr Glu Gln Arg
225                 230                 235                 240

Gly Leu Asn Leu Trp Glu Met Ala Glu Phe Leu Arg Gln Gln Asp Val
                245                 250                 255

Val Asn Ala Ile Asn Leu Asp Gly Gly Gly Ser Ala Thr Phe Val Leu
            260                 265                 270

Asn Gly Thr Leu Ala Ser Tyr Pro Ser Asp His Cys Gln Asp Asn Met
        275                 280                 285

Trp Arg Cys Pro Arg Gln Val Ser Thr Val Cys Val His Glu Pro
290                 295                 300

Arg Cys Gln Pro Pro Asp Cys Ser Gly His Gly Thr Cys Val Asp Gly
305                 310                 315                 320

His Cys Glu Cys Thr Ser His Phe Trp Arg Gly Glu Ala Cys Ser Glu
                325                 330                 335

Leu Asp Cys Gly Pro Ser Asn Cys Ser Gln His Gly Leu Cys Thr Ala
            340                 345                 350

Gly Cys His Cys Asp Ala Gly Trp Thr Gly Ser Asn Cys Ser Glu Glu
        355                 360                 365

Cys Pro Leu Gly Trp Tyr Gly Pro Gly Cys Gln Arg Pro Cys Gln Cys
370                 375                 380

Glu His Gln Cys Phe Cys Asp Pro Gln Thr Gly Asn Cys Ser Ile Ser
```

```
                385             390             395             400
Gln Val Arg Gln Cys Leu Gln Pro Thr Glu Ala Thr Pro Arg Ala Gly
                405                 410                 415
Glu Leu Ala Ser Phe Thr Arg Thr Thr Trp Leu Ala Leu Thr Leu Thr
                420                 425                 430
Leu Ile Phe Leu Leu Leu Ile Ser Thr Gly Val Asn Val Ser Leu Phe
            435                 440                 445
Leu Gly Ser Arg Ala Glu Arg Asn Arg His Leu Asp Gly Asp Tyr Val
    450                 455                 460
Tyr His Pro Leu Gln Glu Val Asn Gly Glu Ala Leu Thr Ala Glu Lys
465                 470                 475                 480
Glu His Met Glu Glu Thr Ser Asn Pro Phe Lys Asp
                485                 490

<210> SEQ ID NO 21
<211> LENGTH: 9792
<212> TYPE: DNA
<213> ORGANISM: Mus musculus

<400> SEQUENCE: 21
caggctcggg acttactata acacaggaca cttgtcacct gaaagcttga gtcagtcagt      60
tattatggtc tgtgtgtgag atacaagtgg gtgcataggc agtggtgcac acatgtagat     120
cagactttct acagccaatt ctcttcttcc tcctctccat gggttcaggg tcttcatctc     180
aggttgcaca gcgagttcat ttatgtgctg tgccatctcg ccagtcgttc ctatatccta     240
gaggaaaact agtttcttct ggtcaagagg aggaaagagt ggagacctgt cattctaaga     300
tacccaaaac agggccaggt tggggacctg tgcctttaat cccatcactt ggggattagg     360
tagaagcaag aggctctaga ccagtctaca cactgaattt caagccagcc tacctataaa     420
tcagagaccc tgcttcaaaa ataaaattaa acaaaaacga agataaacca agctacccaa     480
aacacaagag ttaatccagt cagacaggtc tagcaaatgc taggatgaaa ggtgtgcacc     540
accacgagtg ggctgcaagc ctctctctct ctctctctct ctctctctct ctcgtttgtt     600
ttgttttttcg agacaaggtt tctctgtgta gccctggctg tcctggaact cactctgtag     660
accaggctgg cctcgagctt cactcttaaa agttcctctt cctcctcctc catcttttcc     720
tcctcttacc ccctaggctc cttttcctct tcttgtcttt cagataaagt ctcaagtagt     780
ccagactggt ctcaaactaa ctaactagcc aagaatagcc aacctcttaa cttccgattc     840
tcctgcctct gctgaatgct ggggttgtgg cgtgggccac cacttctggt ttgtgcaaca     900
cagaaggaac tagggcttta agcacgagaa gcaagttctg tacagactta cacaggccca     960
gcatctgttc ttgcaatttt ctgtaagttt gacataatat gagaataaaa agctatctat    1020
ctcccttcca gccttaccct ctctgatgga attcgaatgc gtaatcaaag cacccaacag    1080
cctggcctga atcacgtggg gcaagcccca cgtgaccgga gcaccaatcc aatatggcgg    1140
cgcccagggg gcccgggctg ttcctcatac ccgcgctgct cggcttactc ggggtggcgt    1200
ggtgcagctt aagcttcggg tgagtgcaag ccgccgggc cagcctggct ggggtccacc    1260
tttcctgagc gctctcaggc acagccctcc gacctcacga tcgccccgtc cctgcagggt    1320
ttccgcgac gatgacctgc tgctgcctta cccactagcg cgcagacgtc cctcgcgaga    1380
ctgcgcccgg gtgcgctcag gtagcccaga gcaggagagc tggcctccgc cacctctggc    1440
cacccacgaa ccccgggcgc caagccacca cgcggccgtg cgcaccttcg tgtcgcactt    1500
cgaggggcgc gcggtggccg ccacctgac gcgggtcgcc gatcccctac gcactttctc    1560
```

-continued

```
ggtgctggag cccggaggag ccggggctg cggcggcaga agcgccgcgg ctactgtgga    1620
ggacacagcc gtccgggccg gttgccgcat cgctcagaac ggtggcttct tccgcatgag    1680
cactggcgag tgcttgggga acgtggtgag cgacgggcgg ctggtgagca gctcaggggg    1740
actgcagaac gcgcagttcg gtatccgacg cgatggaacc atagtcaccg ggtgaggagg    1800
cagggagccc cggggctgta gagggcaaag ggtctctgat gttctttcag agccatgcct    1860
ccgagtccag gtccctaacc aaacttcctg tctttcttct tccgagtaat gacgctgaca    1920
ccttccttcc tttaagttta ttcatgtgcc actgaataat ctgtgatcag gccgtgtgtg    1980
gggacttggg gaggcgaccg tgagcctgaa cacagtttgt gccctagtga actttgtgta    2040
gtattagaga aacatttcgt gttcaacgaa gccatggaac caattggaaa tagtgtagag    2100
tttatggagc agtcccagac agctagctgg aggccttttg ctgtcctgat aaaaatccag    2160
gttagacaag gagcttgttg agggcagcct ttggaagttt ctgtgtttct tgaaatttga    2220
cagcagccag agttgacagc aggcaggcag gagtagaagg tagcgccatc tggtgttcca    2280
gttctcttcc aaggttccgt tttttgccaa ggctgggaag tgggctttcc ccaactcttc    2340
tcagcccttg gttgcaattt ctgggcctgc ccatgtatct ggttcttcat ccttcaacat    2400
cagccagtgt caccactgtt gatcttaggt tttcacagat cctaaaactt ctgccagtga    2460
ccagcgcctg cagtttctct tccctggctc tgtccttcaa cctctctaca ttccagccat    2520
ctccctagct cctctcttgg actccctttc agacttgttg tcatgatcac tgtctcagaa    2580
cccctattgc tcctttacaa tggtccactg acctgctcac ctcctacttt tttttttaa    2640 atgtgtgtgc atctgtgtgt gcctgagggg agaccagagt ttgatttcaa atgtcttcta    2700
ttctcttttc ctccatctta ttttctaaca caaaatctga atctagagat cactggttca    2760
gttaacctgg ctggccggta accccaggg ccctcctgct tccctctgtc caccccaccc     2820
cagcactaag gctacagtgt gtgctgttcc agccagcttt tcatgggtg ctgaggatct     2880 gaacgcaggt tcacatgtgt ggtgggaagg cttttaccca atgctctgtc tttccagccc    2940
atcctccctt gttaactgcc aaacagctgc ctatcctgtc catgtgtagc tcactgctac    3000 ttctttatt atgaggtcag cacatgttac taaagatggc aagagaagaa ggttctttca    3060
ttgtgtcata gctatagctc aggaggaatt ttatttcctg tgtaggcaca caggagagca    3120
tcttccagct cacactccaa ctgaactaac tgaacacctg cctatatatc caaagaaggg    3180
gtgtcagtgc caatcacagc acacctccag tgcaaatgaa ggtttgtgtt tgcaccaatc    3240
acagccttgc ctctttagc atgcatcaca acaaagtcct cctagactat cagggatat     3300 gctctcttgg ccaaggtagg aatagttgca gtgtcatctg gcacaaacca tttcaaacgg    3360
cctggctgag gttatgcctt cgggaacctg aagtctttgt gtggttgtct ccaagtgtct    3420
gtggagctcc aggcggctgg tgctgacaga cgctttgtct agttggctgt ttgactttg     3480 cttaagcagc cagggcagta gagtctaaca gatgctaatt tcaggatcag gaagactgta    3540
gaaaaatgag catcaagaag cccctggtac ccaaagctgc tcttgccaat gagtgaacct    3600
ctgccttccc gcttccaggt cctgtcttga agaagaggtt ctggatcccg tgaatccgtt    3660
cgtgcagctg ctgagcggag tcgtgtggct catccgcaat ggaaacatct acatcaacga    3720
gagccaagcc atcgagtgtg acgagacaca ggagacaggt caggaagcac aggtgttctg    3780
ttttatttgt attaggtttt gatttgttta ttttgtgcat gcagcgggtg catgcatgct    3840
cctttccttt cgccatgtga gtcctgagta ttgaactcag actgttaagt gtgatgggag    3900
```

-continued

| | |
|---|---|
| gcactttacc cactgagcca ctttcccagc cctcagcatc agctttcttc agacccagga | 3960 |
| acagtgtgag tgggttattc tttagtgttc ccaaacattt actgagcagc tatttactgt | 4020 |
| ttagcactat ggtgagagtc ctagggattc agtcttatgt agaatataga aggagaatcc | 4080 |
| ttggcaataa gctggaaaat tgtgacaagt gccaagaaag aaacaggaga aaggggaccg | 4140 |
| gtggggacca gaagcacagg tatgaggaaa gtgcctgcag atttgctgta tggtggcctc | 4200 |
| cacatggcct aggagtttgt cataaatgca gagccatgag tccaccctcc ctatacctcc | 4260 |
| catccagaaa ccactggtta atcctaaca acttgggtgt gcaggcactc ccttggtgac | 4320 |
| tctgatggac actcaaggtc aagggccact ggggatggg ctgatgagtt ggcttggtca | 4380 |
| gtaaagtatt tgccttgaaa gtgtgaggac ctgagttgga ccccagaaa gaaacattaa | 4440 |
| aagccaagtg ctgggatgca cacttgcatt cccaggatg gagctggaag cagggatag | 4500 |
| gcagatccac ggccacacgg tgatattcta agctaacaag agacctgtct cacacagaaa | 4560 |
| gtgggtggca cctgaggacc aacacccagg gttatcctct gacgtacctc cagagtggaa | 4620 |
| aatactgggg tggtggaaaa ggacactttg gtcctgggaa tctggctatt cagggtatag | 4680 |
| tgtagaggga gagggagact caagaggctg tctttgagtc aaaggaacaa gctatcagaa | 4740 |
| gaactcaggg cagaggcctg tggttcccag gctcagggca gccttcaagg ccctaggcag | 4800 |
| agagtagctg ctgggtgaac aagtacagaa gtgaggcctg gggcctcagg caaggcctgt | 4860 |
| gaaatccttc caccaacata aagtttctg gagactgaga tcacatgaag tgcttctggc | 4920 |
| tgtggcatgg aagctcactg gaggtggagc tgggatgtgg ctcagtgatc cagtgcttgc | 4980 |
| cacacgtgca cgagggaagg agccatcaaa agagagaaag tcgggagacc tgagggtcc | 5040 |
| cctggagagc tgggtaacca ccccgggccc ttctccttta ggttctttta gcaaatttgt | 5100 |
| gaatgtgatg tcagccagga cagccgtggg tcatgaccgt gaggggcagc ttatcctctt | 5160 |
| ccatgctgat ggacagacgg aacagcgtgg tgagtcccag gaaccttggg gctgtttgca | 5220 |
| cttcagccac cctacctttc cagtcggttc tggggtattg gtgggacaag acagctttcc | 5280 |
| ggccattttg gaagtttcat ctggaggcaa tagcatttac ctactagtga agaagccag | 5340 |
| ttaagccaga gaccacaggg gctcaagctg catacccct ctgcacagcc ttaacctatg | 5400 |
| ggagatggca gagttcctgc gtcaacaaga tgtcgtcaat gccatcaacc tggatggagg | 5460 |
| cggttctgct acttttgtgc tcaatgggac cctggccagt tacccttcag atcactggta | 5520 |
| agaacccttg agccacctt gtggctctct cagactgtct cactcagtca atactgagac | 5580 |
| cctgttgtgt gccaggccct gggtatccaa aagtgagcag aagagccgag atctcttccc | 5640 |
| tcagggtgct gcacagccca tccctggaaa cctgagacag gtcaggaaag gcctccctga | 5700 |
| ggacagtgaa gtaagacctg aggagatggc tggccggggt tgagagagcc tttaccggaa | 5760 |
| gacaaactgt acgcaatggg gaaatccgct aagtggccca gggagaggct ggagctatag | 5820 |
| ctcaggagga aaagtacttg cctcgcaagc gaaggacctg agtttaaact ccaaaaccca | 5880 |
| tataaaaagc cagatacgag caagtggcac atgcttgcag tcccagcctt gttgaggaag | 5940 |
| agtcaggtga atcctgaccc tctgccagc cagcctagcc tacttttggg caaggtccag | 6000 |
| gccagcgaga aagataaata aaataaagtt ttaaatgaca tgtatctaag gttgtcctga | 6060 |
| ctccatatgc gcacgcacgc atgcacgcac gcacaactgg cagaatgaa agggaggcaa | 6120 |
| actggacagc ctttataggc tgcggcaggg accagcacca aggcctagac ctcgtctcac | 6180 |
| agtgaatccc ccacagccag acaaacatgt ggcgctgtcc ccgccaagtg tccactgtgg | 6240 |
| tgtgtgtgca tgaaccgcgc tgccagccac ccgactgcag tggccatggg acctgtgtgg | 6300 |

```
atggccactg tgaatgcacc agccacttct ggcggggcga ggcctgcagc gagctggact   6360
gtggcccctc caactgcagc cagcatgggc tgtgcacaga gagtgagtgg ggagcccaca   6420
ggagggtggt gctctggcgg gaccccagct cgcccatgct agactcccgc ctgtgtcctt   6480
acccagcctc tgtggtcttg ctttggtagc tggctgccac tgtgatgctg ggtggacagg   6540
atccaactgc agtgaaggtg agagctgcct gcaaacactc ctggagaggg tggcctggct   6600
gcacgcagct ggtatgacgc cttcgtccct ccttctggct tggaacttac cttcagagcc   6660
ttttctcatt tcgcatgtgg atacccgatg ttctacctac tgaaagagcc acaagtagg    6720 aagccagatt ttcagtattg tcactcaact ctaaggacca atagcaaaaa acaaagtgg    6780 ccacgcccct gagggagatc caccaaagtc cttaactcct ggaaagcagc tcctggtgat   6840
cctaggcatg ggtagggtgg tttcagcatc agctcagtgg agttcccatt cataatttct   6900 tcatccttt aaggtcataa gttctagagc ccaccttaaa tctaggcagt attcttggtg    6960
tttatctgag acaaagtctt atacagccca cgcagttctc taacttagta tgtaaccgag   7020
aatggcctca agcaacctgc ttcctccttt caagcgctgg gattataggc atagcaccaa   7080
cttatagggt gctagaagtc aaacccaggg ccctatgtat atgcagcaag cactctagaa   7140
actggaacac agccctgttt gcagcccggt taccttggag ggttgggtcc cagggatctg   7200
agggcatctc cttcagcatg gccatgtgca cacccaggag ccaggctgtc tgtgacagga   7260
gaccatgcca cccaaggtga gacctccctg ccaccatctc ctctccacag agtgtcctct   7320
gggctggtat gggccaggtt gccagaggcc ctgccagtgt gagcaccagt gtttctgtga   7380
cccgcagact ggcaactgca gcatctccca aggtatgcgg ccttaaaggt tcttgagctg   7440
ggagcccttg gggcaggtct ggggtaggtg gactctcccc agcccttctt tctggtgtct   7500
tgcagtgagg cagtgtctcc agccaactga ggctacgccg agggcaggag agctggcctc   7560
tttcaccagg taagtgtttt agcaggcact gagcccctat gtctcatccg tgaggcacta   7620
gccaggccag gaggtcacag gttaccctct actttgcaag ctcagggaca gtcacaggta   7680
aaactggcat ccaggaaaga ccctgagcta cccagtggaa ctcaaaggta gcaggctatg   7740
ggtgtcatgc ctctggctgc agagactcca cttagatgct ggagcagggc catagagaca   7800
ggaaggactc accttatttc tgaactcttc cgtgtgttca ggctttgtgt tgttgttgct   7860
tcctttctgc tgtttcctgg gtttccagct ccatccccac agggctcatg gaaagaattg   7920
tgaagcaggg ggtgtggctc aattggcaga ttgattgcct ggcatgcaga aagccctagg   7980
ttcaatcccc agcatttcat atcataaccc aggcatggtg gcatcatgtg cctgtaagtc   8040
cagcacttgg gaggtagaag cagaaaagcc acgagtttaa gaatgttagg gagtcttagg   8100
ccaacctggg ataccctaaga caagagatag atgtagggag atagattgac agacagacag   8160
acagacagac agacagacag atcttgagct ggaccttctg gcacaagcct gtcatcctag   8220
ctattccagg aagctgaagc aggaagatag caaattcaag gccagcttaa gccacagatt   8280
gagttcaaga tcaacctgag caactttatg aaatcctatt ataacataaa agtaggggt    8340 gggaggttag gctgtagctc agtggtagag tgattgccta gcacgcacaa gacccaggtt   8400
caattcccag tactgcaaaa aatatattag gaaccccta aaagcagtaa cattcacatt    8460
agatgtgtgt gtgtgtgtgt gtgtgtgtgt gtgtgtgtgt gtgtgtgtgt gtgtgttttg   8520
ttgggtattt atttcattta catttccaat gctatcccaa aagtccccca catcctcccc   8580
cacccaccac cttgtttttt ttttttttt  tttttttttt tttgacctga aactcacagg   8640
```

```
ttaggttaga caagctgact ggtgagctcc aacttccaac gtaccatcat gcctggcttt    8700
tgttttggtg tctctgtgta accctggatg tcctggagct ctctctgtag accagcctgg    8760
ccttaaactc acagaaaccc acctgtttct gcctcccatg tgctgggatt aaaggcgtgt    8820
gccacctcac ccagccctgc tggacttaaa ttgggtcttc attttataag acaagcatga    8880
gctaattccc cagttcctaa aatgtttta acatccttaa acatcagaga ctgtctgtgg     8940
tattccctcc atgtgtcttc agtataccta ctcccctccc tgcctactgg gttcaacatg    9000
cccagtttgg gttctggctg cctgccccca ctcaagactc tcttttccat ctcaggacca    9060
cctggctagc cctcaccctg acactaattt tcctgctgct gatcagcact ggggtcaacg    9120
tgtccttgtt cctgggctcc agggccgaga ggaaccggca cctcgacggg gactatgtgt    9180
atcacccact gcaggaggtg aacgggaag cgctgactgc agagaaggag cacatggagg     9240
aaactagcaa ccccttcaag gactgaagag ctgccccaac ggcatgctcc agataatctt    9300
gtccctgctc ctcacttcca caggggacat tgtgaggcca ctggcatgga tgctatgcac    9360
cccacccttt gctggccata ttcctcctgt ccccatgctg tggctcatgc caacctagca    9420
ataaggagct ctggagagcc tgcacctgcc tcccgctcgc ctatatctgc tgcccagagg    9480
cctgtctcgc acagggtct cgccactgcc aaagactccc aggaagtcaa agactcccag     9540
taatccacta gcaaatggaa ctctgtaacg ccatcataac aagagtggcc actctccgcg    9600
tgcacaggta tgaaatataa atccttacac acacacacac acacaccctc ggctcagcca    9660
cggcactcgc cttttataca gcgtcatcgc tggacagcca actagaactc tgcatcctgt    9720
cacaggaagc acctcataag aaggaatggg gagggaaggc agtcgccttg ttttcagacc    9780
ttagccgaat tc                                                        9792
```

<210> SEQ ID NO 22
<211> LENGTH: 4
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (2)..(2)
<223> OTHER INFORMATION: Xaa is any amino acid
<221> NAME/KEY: misc_feature
<222> LOCATION: (3)..(3)
<223> OTHER INFORMATION: Xaa is any amino acid

<400> SEQUENCE: 22

Arg Xaa Xaa Arg
1